United States Patent [19]
Kishimoto et al.

[11] Patent Number: 5,844,082
[45] Date of Patent: Dec. 1, 1998

[54] HUMAN ACUTE PHASE RESPONSE FACTOR

[75] Inventors: Tadamitsu Kishimoto, 3-5-31, Nakanocho, Tondabayashi-shi; Shizuo Akira, both of Osaka, Japan

[73] Assignee: Tadamitsu Kishimoto, Osaka, Japan

[21] Appl. No.: 965,462

[22] Filed: Nov. 6, 1997

Related U.S. Application Data

[62] Division of Ser. No. 416,581, Apr. 4, 1995, Pat. No. 5,719,042.

[30] Foreign Application Priority Data

Apr. 4, 1994 [JP] Japan ........................................ 6-65825

[51] Int. Cl.$^6$ .................................................... C07K 14/47
[52] U.S. Cl. ................................................................ 530/350
[58] Field of Search ............................................. 530/350

[56] References Cited

FOREIGN PATENT DOCUMENTS 9319179  9/1993  WIPO .
9508629  3/1995  WIPO .

OTHER PUBLICATIONS

Yuan, J. et al., "The Signalling pathways of interleukin–6 and gamma interferon convorge by the activation of different transcription factors", *Mol Cell Biol*, 14(3), pp. 1657–1668, Mar. 1994.

Lutticken, C. et al., "Association of transcription factor APRF and protein kinase Jaki with the interleukin–6 signal transducer gp130", *Science*, 263(5143), pp. 89–92. 7 Jan. 1994.

Raz, R. et al., "Acute–Phase Response Factor and Additional Members of the Interferom–Stimulated Gene Factor–s", *Jour Of Biological Chem.* 269, pp. 24391–24395, 1994, "Trying on a New Pair of SH2s", Montminy, Science,vol. 261, Sep. 1993, pp. 1694–1695.

"A nuclear factor for IL–6 . . . ", Akira et al., The EMBO Journal, vol. 9, No. 6, pp. 1897–1906, 1990.

"IL–6DBP, a Nuclear Protein . . .", Poli et al. Cell, vol. 63, pp. 643–653, 1990.

"A member of the C/EBP family . . .", Kinoshita et al., Proc. Natl. Acad. vol. 89, pp. 1473–1476, 1992.

"Acute–Phase Response Factor", Wegenka et al., Molecular & Cellular Bio., vol. 13, pp. 276–288, 1993.

"Molecular Cloning of APRF . . .", Akira et al., Cell, vol. 77, pp. 63–71. 1994.

"STAT3 activation . . .", Minami et al. PNAS 93:3963, 1996.

"STAT3 and STAT4: Members . . . ", Zhong et al., Proc. Natl Acad. vol. 91, pp. 4806–4810, 1994.

"STAT3: A STAT . . .", Zhong et al., Science, vol. 264, pp. 95–98, 1994.

"The Interleukin–6–Activated. . . ", Wegenka et al., Molec. Cell. Biol., v. 14, pp. 3186–3196, 1994.

"Requirment of Serine. . .", Zhang et al., Science, v. 267, p. 1890, 1995.

*Primary Examiner*—Terry A. McKelvey
*Attorney, Agent, or Firm*—Sughrue, Mion, Zinn, Macpeak & Seas, PLLC

[57] ABSTRACT

Mammal transcription factor APRF, process for the preparation of it, DNAs encoding the product, replication and expression vector comprising the DNA, host cells transformed or tranfected with the replication and expression vector, evaluating and screening method for searching an inhibitory agent on the function of APRF and an inhibitory agent against the function of the APRF. The peptide of the present invention (APRF) may be useful for complement or suppression of the function of APRF, screening an inhibitory agent against the function of APRF. Inhibiting agent containing the product as active ingredient of the present invention may be also useful for treatment of diseases related to cytokine such as IL-6, i.e. inflammatory diseases.

2 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 770 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

```
Met  Ala  Gln  Trp  Asn  Gln  Leu  Gln  Gln  Leu  Asp  Thr  Arg  Tyr  Leu  Glu
 1              5                        10                       15
```

```
Gln  Leu  His  Gln  Leu  Tyr  Ser  Asp  Ser  Phe  Pro  Met  Glu  Leu  Arg  Gln
               20                  25                      30

Phe  Leu  Ala  Pro  Trp  Ile  Glu  Ser  Gln  Asp  Trp  Ala  Tyr  Ala  Ala  Ser
          35                  40                      45

Lys  Glu  Ser  His  Ala  Thr  Leu  Val  Phe  His  Asn  Leu  Leu  Gly  Glu  Ile
     50                       55                      60

Asp  Gln  Gln  Tyr  Ser  Arg  Phe  Leu  Gln  Glu  Ser  Asn  Val  Leu  Tyr  Gln
65                            70                 75                          80

His  Asn  Leu  Arg  Arg  Ile  Lys  Gln  Phe  Leu  Gln  Ser  Arg  Tyr  Leu  Glu
                    85                      90                      95

Lys  Pro  Met  Glu  Ile  Ala  Arg  Ile  Val  Ala  Arg  Cys  Leu  Trp  Glu  Glu
               100                 105                     110

Ser  Arg  Leu  Leu  Gln  Thr  Ala  Ala  Thr  Ala  Ala  Gln  Gln  Gly  Gly  Gln
               115                 120                     125

Ala  Asn  His  Pro  Thr  Ala  Ala  Val  Val  Thr  Glu  Lys  Gln  Gln  Met  Leu
          130                 135                     140

Glu  Gln  His  Leu  Gln  Asp  Val  Arg  Lys  Arg  Val  Gln  Asp  Leu  Glu  Gln
145                           150                     155                     160

Lys  Met  Lys  Val  Val  Glu  Asn  Leu  Gln  Asp  Asp  Phe  Asp  Phe  Asn  Tyr
                    165                      170                     175

Lys  Thr  Leu  Lys  Ser  Gln  Gly  Asp  Met  Gln  Asp  Leu  Asn  Gly  Asn  Asn
               180                      185                     190

Gln  Ser  Val  Thr  Arg  Gln  Lys  Met  Gln  Gln  Leu  Glu  Gln  Met  Leu  Thr
          195                      200                     205

Ala  Leu  Asp  Gln  Met  Arg  Arg  Ser  Ile  Val  Ser  Glu  Leu  Ala  Gly  Leu
     210                      215                     220

Leu  Ser  Ala  Met  Glu  Tyr  Val  Gln  Lys  Thr  Leu  Thr  Asp  Glu  Glu  Leu
225                      230                     235                          240

Ala  Asp  Trp  Lys  Arg  Arg  Gln  Gln  Ile  Ala  Cys  Ile  Gly  Gly  Pro  Pro
                    245                     250                     255

Asn  Ile  Cys  Leu  Asp  Arg  Leu  Glu  Asn  Trp  Ile  Thr  Ser  Leu  Ala  Glu
               260                      265                     270

Ser  Gln  Leu  Gln  Thr  Arg  Gln  Gln  Ile  Lys  Lys  Leu  Glu  Glu  Leu  His
          275                      280                     285

Gln  Lys  Val  Ser  Tyr  Lys  Gly  Asp  Pro  Ile  Val  Gln  His  Arg  Pro  Met
     290                      295                     300

Leu  Glu  Glu  Arg  Ile  Val  Glu  Leu  Phe  Arg  Asn  Leu  Met  Lys  Ser  Ala
305                      310                     315                          320

Phe  Val  Val  Glu  Arg  Gln  Pro  Cys  Met  Pro  Met  His  Pro  Asp  Arg  Pro
               325                      330                     335

Leu  Val  Ile  Lys  Thr  Gly  Val  Gln  Phe  Thr  Thr  Lys  Val  Arg  Leu  Leu
               340                      345                     350

Val  Lys  Phe  Pro  Glu  Leu  Asn  Tyr  Gln  Leu  Lys  Ile  Lys  Val  Cys  Ile
          355                      360                     365

Asp  Lys  Asp  Ser  Gly  Asp  Val  Ala  Ala  Leu  Arg  Gly  Ser  Arg  Lys  Phe
     370                      375                     380

Asn  Ile  Leu  Gly  Thr  Asn  Thr  Lys  Val  Met  Asn  Met  Glu  Glu  Ser  Asn
385                      390                     395                          400

Asn  Gly  Ser  Leu  Ser  Ala  Glu  Phe  Lys  His  Leu  Thr  Leu  Arg  Glu  Gln
               405                      410                     415

Arg  Cys  Gly  Asn  Gly  Gly  Arg  Ala  Asn  Cys  Asp  Ala  Ser  Leu  Ile  Val
                    420                     425                     430

Thr  Glu  Glu  Leu  His  Leu  Ile  Thr  Phe  Glu  Thr  Glu  Val  Tyr  His  Gln
```

|     |     |     |     | 435 |     |     |     | 440 |     |     |     | 445 |     |     |
|-----|-----|-----|-----|-----|-----|-----|-----|-----|-----|-----|-----|-----|-----|-----|

```
Gly  Leu  Lys  Ile  Asp  Leu  Glu  Thr  His  Ser  Leu  Ser  Val  Val  Ile
     450                      455                      460
Ser  Asn  Ile  Cys  Gln  Met  Pro  Asn  Ala  Trp  Ala  Ser  Ile  Leu  Trp  Tyr
465                      470                      475                      480
Asn  Met  Leu  Thr  Asn  Asn  Pro  Lys  Asn  Val  Asn  Phe  Phe  Thr  Lys  Pro
                    485                      490                           495
Pro  Ile  Gly  Thr  Trp  Asp  Gln  Val  Ala  Glu  Val  Leu  Ser  Trp  Gln  Phe
               500                      505                      510
Ser  Ser  Thr  Thr  Lys  Arg  Gly  Leu  Ser  Ile  Glu  Gln  Leu  Thr  Thr  Leu
               515                      520                      525
Ala  Glu  Lys  Leu  Leu  Gly  Pro  Gly  Val  Asn  Tyr  Ser  Gly  Cys  Gln  Ile
     530                      535                      540
Thr  Trp  Ala  Asn  Phe  Cys  Lys  Glu  Asn  Met  Ala  Gly  Lys  Gly  Phe  Ser
545                      550                      555                      560
Tyr  Trp  Val  Trp  Leu  Asp  Asn  Ile  Ile  Asp  Leu  Val  Lys  Lys  Tyr  Ile
                    565                      570                      575
Leu  Ala  Leu  Trp  Asn  Glu  Gly  Tyr  Ile  Met  Gly  Phe  Ile  Ser  Lys  Glu
               580                      585                      590
Arg  Glu  Arg  Ala  Ile  Leu  Ser  Thr  Lys  Pro  Pro  Gly  Thr  Phe  Leu  Leu
               595                      600                      605
Arg  Phe  Ser  Glu  Ser  Ser  Lys  Glu  Gly  Gly  Val  Thr  Phe  Thr  Trp  Val
     610                      615                      620
Glu  Lys  Asp  Ile  Ser  Gly  Lys  Thr  Gln  Ile  Gln  Ser  Val  Glu  Pro  Tyr
625                      630                      635                      640
Thr  Lys  Gln  Gln  Leu  Asn  Asn  Met  Ser  Phe  Ala  Glu  Ile  Ile  Met  Gly
                    645                      650                      655
Tyr  Lys  Ile  Met  Asp  Ala  Thr  Asn  Ile  Leu  Leu  Ser  Pro  Leu  Val  Tyr
               660                      665                      670
Leu  Tyr  Pro  Asp  Ile  Pro  Lys  Glu  Glu  Ala  Phe  Gly  Lys  Tyr  Cys  Arg
          675                      680                      685
Pro  Glu  Ser  Gln  Glu  His  Pro  Glu  Ala  Asp  Pro  Gly  Ser  Ala  Ala  Pro
     690                      695                      700
Tyr  Leu  Lys  Thr  Lys  Phe  Ile  Cys  Val  Thr  Pro  Thr  Thr  Cys  Ser  Asn
705                      710                      715                      720
Thr  Ile  Asp  Leu  Pro  Met  Ser  Pro  Arg  Ala  Leu  Asp  Ser  Leu  Met  Gln
                    725                      730                      735
Phe  Gly  Asn  Asn  Gly  Glu  Gly  Ala  Glu  Pro  Ser  Ala  Gly  Gly  Gln  Phe
               740                      745                      750
Glu  Ser  Leu  Thr  Phe  Asp  Met  Glu  Leu  Thr  Ser  Glu  Cys  Ala  Thr  Ser
          755                      760                      765
Pro  Met
770
```

( 2 ) INFORMATION FOR SEQ ID NO:2:

( i ) SEQUENCE CHARACTERISTICS:
        ( A ) LENGTH: 2310 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:2:

```
ATGGCCCAAT  GGAATCAGCT  ACAGCAGCTT  GACACACGGT  ACCTGGAGCA  GCTCCATCAG        60
```

| | | | | | | |
|---|---|---|---|---|---|---|
| CTCTACAGTG | ACAGCTTCCC | AATGGAGCTG | CGGCAGTTTC | TGGCCCCTTG | GATTGAGAGT | 120 |
| CAAGATTGGG | CATATGCGGC | CAGCAAAGAA | TCACATGCCA | CTTTGGTGTT | TCATAATCTC | 180 |
| CTGGAGAGA | TTGACCAGCA | GTATAGCCGC | TTCCTGCAAG | AGTCGAATGT | TCTCTATCAG | 240 |
| CACAATCTAC | GAAGAATCAA | GCAGTTTCTT | CAGAGCAGGT | ATCTTGAGAA | GCCAATGGAG | 300 |
| ATTGCCCGGA | TTGTGGCCCG | GTGCCTGTGG | GAAGAATCAC | GCCTTCTACA | GACTGCAGCC | 360 |
| ACTGCGGCCC | AGCAAGGGGG | CCAGGCCAAC | CACCCACAG | CAGCCGTGGT | GACGGAGAAG | 420 |
| CAGCAGATGC | TGGAGCAGCA | CCTTCAGGAT | GTCCGGAAGA | GAGTGCAGGA | TCTAGAACAG | 480 |
| AAAATGAAAG | TGGTAGAGAA | TCTCCAGGAT | GACTTTGATT | TCAACTATAA | AACCCTCAAG | 540 |
| AGTCAAGGAG | ACATGCAAGA | TCTGAATGGA | AACAACCAGT | CAGTGACCAG | GCAGAAGATG | 600 |
| CAGCAGCTGG | AACAGATGCT | CACTGCGCTG | GACCAGATGC | GGAGAAGCAT | CGTGAGTGAG | 660 |
| CTGGCGGGGC | TTTTGTCAGC | GATGGAGTAC | GTGCAGAAAA | CTCTCACGGA | CGAGGAGCTG | 720 |
| GCTGACTGGA | AGAGGCGGCA | ACAGATTGCC | TGCATTGGAG | GCCGCCCAA | CATCTGCCTA | 780 |
| GATCGGCTAG | AAAACTGGAT | AACGTCATTA | GCAGAATCTC | AACTTCAGAC | CCGTCAACAA | 840 |
| ATTAAGAAAC | TGGAGGAGTT | GCACCAAAAA | GTTTCCTACA | AAGGGGACCC | CATTGTACAG | 900 |
| CACCGGCCGA | TGCTGGAGGA | GAGGATCGTG | GAGCTGTTCA | GAAACTTAAT | GAAAAGTGCC | 960 |
| TTTGTGGTGG | AGCGGCAGCC | CTGCATGCCC | ATGCATCCTG | ACCGGCCCCT | CGTCATCAAG | 1020 |
| ACCGGCGTCC | AGTTCACTAC | TAAAGTCAGG | TTGCTGGTCA | AGTTCCCTGA | GTTGAATTAT | 1080 |
| CAGCTTAAAA | TTAAAGTGTG | CATTGACAAA | GACTCTGGGG | ACGTTGCAGC | TCTCAGAGGA | 1140 |
| TCCCGGAAAT | TTAACATTCT | GGGCACAAAC | ACAAAAGTGA | TGAACATGGA | AGAATCCAAC | 1200 |
| AACGGCAGCC | TCTCTGCAGA | ATTCAAACAC | TTGACCCTGA | GGGAGCAGAG | ATGTGGGAAT | 1260 |
| GGGGGCCGAG | CCAATTGTGA | TGCTTCCCTG | ATTGTGACTG | AGGAGCTGCA | CCTGATCACC | 1320 |
| TTTGAGACCG | AGGTGTATCA | CCAAGGTCTC | AAGATTGACC | TAGAGACCCA | CTCCTTGTCA | 1380 |
| GTTGTGGTGA | TCTCCAACAT | CTGTCAGATG | CCAAATGCCT | GGGCGTCCAT | CCTGTGGTAC | 1440 |
| AACATGCTGA | CCAACAATCC | CAAGAATGTG | AACTTCTTCA | CTAAGCCGCC | AATTGGAACC | 1500 |
| TGGGACCAAG | TGGCCGAGGT | GCTCAGCTGG | CAGTTCTCGT | CCACCACCAA | GCGGGGGCTG | 1560 |
| AGCATCGAGC | AGCTGACAAC | GCTGGCTGAG | AAGCTCCTAG | GGCCTGGTGT | GAACTACTCA | 1620 |
| GGGTGTCAGA | TCACATGGGC | TAACTTCTGC | AAAGAAAACA | TGGCTGGCAA | GGGCTTCTCC | 1680 |
| TACTGGGTCT | GGCTAGACAA | TATCATCGAC | CTTGTGAAAA | AGTATATCTT | GGCCCTTTGG | 1740 |
| AATGAAGGGT | ACATCATGGG | TTTCATCAGC | AAGGAGCGGG | AGCGGGCCAT | CTTGAGCACT | 1800 |
| AAGCCCCCAG | GCACCTTCCT | GCTGCGCTTC | AGTGAAAGCA | GCAAAGAAGG | AGGCGTCACT | 1860 |
| TTCACTTGGG | TGGAGAAGGA | CATCAGCGGT | AAGACCCAGA | TCCAGTCCGT | GGAACCATAC | 1920 |
| ACAAAGCAGC | AGCTGAACAA | CATGTCATTT | GCTGAAATCA | TCATGGGCTA | TAAGATCATG | 1980 |
| GATGCTACCA | ATATCCTGTT | GTCTCCACTT | GTCTATCTCT | ATCCTGACAT | TCCCAAGGAG | 2040 |
| GAGGCATTCG | GAAGTATTG | TCGGCAGAG | AGCCAGGAGC | ATCCTGAAGC | TGACCCAGGT | 2100 |
| AGCGCTGCCC | CATACCTGAA | GACCAAGTTT | ATCTGTGTGA | CACCAACGAC | CTGCAGCAAT | 2160 |
| ACCATTGACC | TGCCGATGTC | CCCCCGCGCT | TTAGATTCAT | TGATGCAGTT | TGGAAATAAT | 2220 |
| GGTGAAGGTG | CTGAACCCTC | AGCAGGAGGG | CAGTTTGAGT | CCCTCACCTT | TGACATGGAG | 2280 |
| TTGACCTCGG | AGTGCGCTAC | CTCCCCCATG | | | | 2310 |

( 2 ) INFORMATION FOR SEQ ID NO:3:

( i ) SEQUENCE CHARACTERISTICS:

(A) LENGTH: 2787 base pairs
(B) TYPE: nucleic acid
(C) STRANDEDNESS: single
(D) TOPOLOGY: linear (ii) MOLECULE TYPE: cDNA to mRNA (xi) SEQUENCE DESCRIPTION: SEQ ID NO:3:

| | | | | | |
|---|---|---|---|---|---|
| CAGCTGGAAT | TCGGGGCGGC | GGCGCAGACT | GGGAGGGGGA | GCCGGGGGTT | CCGACGTCGC 60 |
| AGCCGAGGGA | ACAAGCCCCA | ACCGGATCCT | GGACAGGCAC | CCCGGCTTGG | CGCTGTCTCT 120 |
| CCCCCTCGGC | TCGGAGAGGC | CCTTCGGCCT | GAGGGAGCCT | CGCCGCCCGT | CCCCGGCACA 180 |
| CGCGCAGCCC | CGGCCTCTCG | GCCTCTGCCG | GAGAAACAGG | ATGGCCCAAT | GGAATCAGCT 240 |
| ACAGCAGCTT | GACACACGGT | ACCTGGAGCA | GCTCCATCAG | CTCTACAGTG | ACAGCTTCCC 300 |
| AATGGAGCTG | CGGCAGTTTC | TGGCCCCTTG | GATTGAGAGT | CAAGATTGGG | CATATGCGGC 360 |
| CAGCAAAGAA | TCACATGCCA | CTTTGGTGTT | TCATAATCTC | CTGGGAGAGA | TTGACCAGCA 420 |
| GTATAGCCGC | TTCCTGCAAG | AGTCGAATGT | TCTCTATCAG | CACAATCTAC | GAAGAATCAA 480 |
| GCAGTTTCTT | CAGAGCAGGT | ATCTTGAGAA | GCCAATGGAG | ATTGCCCGGA | TTGTGGCCCG 540 |
| GTGCCTGTGG | GAAGAATCAC | GCCTTCTACA | GACTGCAGCC | ACTGCGGCCC | AGCAAGGGGG 600 |
| CCAGGCCAAC | CACCCCACAG | CAGCCGTGGT | GACGGAGAAG | CAGCAGATGC | TGGAGCAGCA 660 |
| CCTTCAGGAT | GTCCGGAAGA | GAGTGCAGGA | TCTAGAACAG | AAAATGAAAG | TGGTAGAGAA 720 |
| TCTCCAGGAT | GACTTTGATT | TCAACTATAA | AACCCTCAAG | AGTCAAGGAG | ACATGCAAGA 780 |
| TCTGAATGGA | AACAACCAGT | CAGTGACCAG | GCAGAAGATG | CAGCAGCTGG | AACAGATGCT 840 |
| CACTGCGCTG | GACCAGATGC | GGAGAAGCAT | CGTGAGTGAG | CTGGCGGGGC | TTTTGTCAGC 900 |
| GATGGAGTAC | GTGCAGAAAA | CTCTCACGGA | CGAGGAGCTG | GCTGACTGGA | AGAGGCGGCA 960 |
| ACAGATTGCC | TGCATTGGAG | GCCCGCCCAA | CATCTGCCTA | GATCGGCTAG | AAAACTGGAT 1020 |
| AACGTCATTA | GCAGAATCTC | AACTTCAGAC | CCGTCAACAA | ATTAAGAAAC | TGGAGGAGTT 1080 |
| GCACCAAAAA | GTTTCCTACA | AAGGGGACCC | CATTGTACAG | CACCGGCCGA | TGCTGGAGGA 1140 |
| GAGGATCGTG | GAGCTGTTCA | GAAACTTAAT | GAAAAGTGCC | TTTGTGGTGG | AGCGGCAGCC 1200 |
| CTGCATGCCC | ATGCATCCTG | ACCGGCCCCT | CGTCATCAAG | ACCGGCGTCC | AGTTCACTAC 1260 |
| TAAAGTCAGG | TTGCTGGTCA | AGTTCCCTGA | GTTGAATTAT | CAGCTTAAAA | TTAAAGTGTG 1320 |
| CATTGACAAA | GACTCTGGGG | ACGTTGCAGC | TCTCAGAGGA | TCCCGGAAAT | TTAACATTCT 1380 |
| GGGCACAAAC | ACAAAAGTGA | TGAACATGGA | AGAATCCAAC | AACGGCAGCC | TCTCTGCAGA 1440 |
| ATTCAAACAC | TTGACCCTGA | GGGAGCAGAG | ATGTGGGAAT | GGGGCCGAG | CCAATTGTGA 1500 |
| TGCTTCCCTG | ATTGTGACTG | AGGAGCTGCA | CCTGATCACC | TTTGAGACCG | AGGTGTATCA 1560 |
| CCAAGGTCTC | AAGATTGACC | TAGAGACCCA | CTCCTTGTCA | GTTGTGGTGA | TCTCCAACAT 1620 |
| CTGTCAGATG | CCAAATGCCT | GGGCGTCCAT | CCTGTGGTAC | AACATGCTGA | CCAACAATCC 1680 |
| CAAGAATGTG | AACTTCTTCA | CTAAGCCGCC | AATTGGAACC | TGGGACCAAG | TGGCCGAGGT 1740 |
| GCTCAGCTGG | CAGTTCTCGT | CCACCACCAA | GCGGGGGCTG | AGCATCGAGC | AGCTGACAAC 1800 |
| GCTGGCTGAG | AAGCTCCTAG | GGCCTGGTGT | GAACTACTCA | GGGTGTCAGA | TCACATGGGC 1860 |
| TAACTTCTGC | AAAGAAAACA | TGGCTGGCAA | GGGCTTCTCC | TACTGGGTCT | GGCTAGACAA 1920 |
| TATCATCGAC | CTTGTGAAAA | AGTATATCTT | GGCCCTTTGG | AATGAAGGGT | ACATCATGGG 1980 |
| TTTCATCAGC | AAGGAGCGGG | AGCGGGCCAT | CTTGAGCACT | AAGCCCCAG | GCACCTTCCT 2040 |
| GCTGCGCTTC | AGTGAAAGCA | GCAAAGAAGG | AGGCGTCACT | TTCACTTGGG | TGGAGAAGGA 2100 |
| CATCAGCGGT | AAGACCCAGA | TCCAGTCCGT | GGAACCATAC | ACAAAGCAGC | AGCTGAACAA 2160 |

-continued

| | | | | | |
|---|---|---|---|---|---|
| CATGTCATTT | GCTGAAATCA | TCATGGGCTA | TAAGATCATG | GATGCTACCA | ATATCCTGTT | 2220
| GTCTCCACTT | GTCTATCTCT | ATCCTGACAT | TCCCAAGGAG | GAGGCATTCG | GGAAGTATTG | 2280
| TCGGCCAGAG | AGCCAGGAGC | ATCCTGAAGC | TGACCCAGGT | AGCGCTGCCC | CATACCTGAA | 2340
| GACCAAGTTT | ATCTGTGTGA | CACCAACGAC | CTGCAGCAAT | ACCATTGACC | TGCCGATGTC | 2400
| CCCCCGCGCT | TTAGATTCAT | TGATGCAGTT | TGGAAATAAT | GGTGAAGGTG | CTGAACCCTC | 2460
| AGCAGGAGGG | CAGTTTGAGT | CCCTCACCTT | TGACATGGAG | TTGACCTCGG | AGTGCGCTAC | 2520
| CTCCCCCATG | TGAGGAGCTG | AGAACGGAAG | CTGCAGAAAG | ATACGACTGA | GGCGCCTACC | 2580
| TGCATTCTGC | CACCCCTCAC | ACAGCCAAAC | CCCAGATCAT | CTGAAACTAC | TAACTTTGTG | 2640
| GTTCCAGATT | TTTTTTAATC | TCCTACTTCT | GCTATCTTTG | AGCAATCTGG | GCACTTTTAA | 2700
| AAATAGAGAA | ATGAGTGAAT | GTGGGTGATC | TGCTTTTATC | TAAATGCAAA | TAAGGATGTG | 2760
| TTCTCTGAGA | CCCATGATCA | GGGGATG | | | | 2787

( 2 ) INFORMATION FOR SEQ ID NO:4:

( i ) SEQUENCE CHARACTERISTICS:
( A ) LENGTH: 2787 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens
( F ) TISSUE TYPE: Placenta ( i x ) FEATURE:
( A ) NAME/KEY: CDS
( B ) LOCATION: 221..2530

( x i ) SEQUENCE DESCRIPTION: SEQ ID NO:4:

| | | | | | |
|---|---|---|---|---|---|
| CAGCTGGAAT | TCGGGGCGGC | GGCGCAGACT | GGGAGGGGGA | GCCGGGGGTT | CCGACGTCGC | 60
| AGCCGAGGGA | ACAAGCCCCA | ACCGGATCCT | GGACAGGCAC | CCCGGCTTGG | CGCTGTCTCT | 120
| CCCCCTCGGC | TCGGAGAGGC | CCTTCGGCCT | GAGGGAGCCT | CGCCGCCCGT | CCCCGGCACA | 180
| CGCGCAGCCC | CGGCCTCTCG | GCCTCTGCCG | GAGAAACAGG | ATG GCC CAA TGG AAT | | 235
| | | | | Met Ala Gln Trp Asn | |
| | | | | 1         5 | |

```
CAG CTA CAG CAG CTT GAC ACA CGG TAC CTG GAG CAG CTC CAT CAG CTC       283
Gln Leu Gln Gln Leu Asp Thr Arg Tyr Leu Glu Gln Leu His Gln Leu
         10                  15                  20

TAC AGT GAC AGC TTC CCA ATG GAG CTG CGG CAG TTT CTG GCC CCT TGG       331
Tyr Ser Asp Ser Phe Pro Met Glu Leu Arg Gln Phe Leu Ala Pro Trp
             25                  30                  35

ATT GAG AGT CAA GAT TGG GCA TAT GCG GCC AGC AAA GAA TCA CAT GCC       379
Ile Glu Ser Gln Asp Trp Ala Tyr Ala Ala Ser Lys Glu Ser His Ala
         40                  45                  50

ACT TTG GTG TTT CAT AAT CTC CTG GGA GAG ATT GAC CAG CAG TAT AGC       427
Thr Leu Val Phe His Asn Leu Leu Gly Glu Ile Asp Gln Gln Tyr Ser
     55                  60                  65

CGC TTC CTG CAA GAG TCG AAT GTT CTC TAT CAG CAC AAT CTA CGA AGA       475
Arg Phe Leu Gln Glu Ser Asn Val Leu Tyr Gln His Asn Leu Arg Arg
 70                  75                  80                  85

ATC AAG CAG TTT CTT CAG AGC AGG TAT CTT GAG AAG CCA ATG GAG ATT       523
Ile Lys Gln Phe Leu Gln Ser Arg Tyr Leu Glu Lys Pro Met Glu Ile
             90                  95                 100

GCC CGG ATT GTG GCC CGG TGC CTG TGG GAA GAA TCA CGC CTT CTA CAG       571
Ala Arg Ile Val Ala Arg Cys Leu Trp Glu Glu Ser Arg Leu Leu Gln
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 105 |     |     |     |     | 110 |     |     |     |     | 115 |     |      |
| ACT | GCA | GCC | ACT | GCG | GCC | CAG | CAA | GGG | GGC | CAG | GCC | AAC | CAC | CCC | ACA | 619  |
| Thr | Ala | Ala | Thr | Ala | Ala | Gln | Gln | Gly | Gly | Gln | Ala | Asn | His | Pro | Thr |      |
|     | 120 |     |     |     |     | 125 |     |     |     |     | 130 |     |     |     |     |      |
| GCA | GCC | GTG | GTG | ACG | GAG | AAG | CAG | CAG | ATG | CTG | GAG | CAG | CAC | CTT | CAG | 667  |
| Ala | Ala | Val | Val | Thr | Glu | Lys | Gln | Gln | Met | Leu | Glu | Gln | His | Leu | Gln |      |
|     | 135 |     |     |     |     | 140 |     |     |     |     | 145 |     |     |     |     |      |
| GAT | GTC | CGG | AAG | AGA | GTG | CAG | GAT | CTA | GAA | CAG | AAA | ATG | AAA | GTG | GTA | 715  |
| Asp | Val | Arg | Lys | Arg | Val | Gln | Asp | Leu | Glu | Gln | Lys | Met | Lys | Val | Val |      |
| 150 |     |     |     |     | 155 |     |     |     |     | 160 |     |     |     |     | 165 |      |
| GAG | AAT | CTC | CAG | GAT | GAC | TTT | GAT | TTC | AAC | TAT | AAA | ACC | CTC | AAG | AGT | 763  |
| Glu | Asn | Leu | Gln | Asp | Asp | Phe | Asp | Phe | Asn | Tyr | Lys | Thr | Leu | Lys | Ser |      |
|     |     |     |     | 170 |     |     |     |     | 175 |     |     |     |     | 180 |     |      |
| CAA | GGA | GAC | ATG | CAA | GAT | CTG | AAT | GGA | AAC | AAC | CAG | TCA | GTG | ACC | AGG | 811  |
| Gln | Gly | Asp | Met | Gln | Asp | Leu | Asn | Gly | Asn | Asn | Gln | Ser | Val | Thr | Arg |      |
|     |     |     | 185 |     |     |     |     |     | 190 |     |     |     |     | 195 |     |      |
| CAG | AAG | ATG | CAG | CAG | CTG | GAA | CAG | ATG | CTC | ACT | GCG | CTG | GAC | CAG | ATG | 859  |
| Gln | Lys | Met | Gln | Gln | Leu | Glu | Gln | Met | Leu | Thr | Ala | Leu | Asp | Gln | Met |      |
|     |     | 200 |     |     |     |     |     | 205 |     |     |     |     | 210 |     |     |      |
| CGG | AGA | AGC | ATC | GTG | AGT | GAG | CTG | GCG | GGG | CTT | TTG | TCA | GCG | ATG | GAG | 907  |
| Arg | Arg | Ser | Ile | Val | Ser | Glu | Leu | Ala | Gly | Leu | Leu | Ser | Ala | Met | Glu |      |
|     | 215 |     |     |     |     |     | 220 |     |     |     |     | 225 |     |     |     |      |
| TAC | GTG | CAG | AAA | ACT | CTC | ACG | GAC | GAG | GAG | CTG | GCT | GAC | TGG | AAG | AGG | 955  |
| Tyr | Val | Gln | Lys | Thr | Leu | Thr | Asp | Glu | Glu | Leu | Ala | Asp | Trp | Lys | Arg |      |
| 230 |     |     |     |     | 235 |     |     |     |     | 240 |     |     |     |     | 245 |      |
| CGG | CAA | CAG | ATT | GCC | TGC | ATT | GGA | GGC | CCG | CCC | AAC | ATC | TGC | CTA | GAT | 1003 |
| Arg | Gln | Gln | Ile | Ala | Cys | Ile | Gly | Gly | Pro | Pro | Asn | Ile | Cys | Leu | Asp |      |
|     |     |     |     | 250 |     |     |     |     | 255 |     |     |     |     | 260 |     |      |
| CGG | CTA | GAA | AAC | TGG | ATA | ACG | TCA | TTA | GCA | GAA | TCT | CAA | CTT | CAG | ACC | 1051 |
| Arg | Leu | Glu | Asn | Trp | Ile | Thr | Ser | Leu | Ala | Glu | Ser | Gln | Leu | Gln | Thr |      |
|     |     |     |     | 265 |     |     |     |     | 270 |     |     |     |     | 275 |     |      |
| CGT | CAA | CAA | ATT | AAG | AAA | CTG | GAG | GAG | TTG | CAC | CAA | AAA | GTT | TCC | TAC | 1099 |
| Arg | Gln | Gln | Ile | Lys | Lys | Leu | Glu | Glu | Leu | His | Gln | Lys | Val | Ser | Tyr |      |
|     |     |     | 280 |     |     |     |     |     | 285 |     |     |     |     | 290 |     |      |
| AAA | GGG | GAC | CCC | ATT | GTA | CAG | CAC | CGG | CCG | ATG | CTG | GAG | GAG | AGG | ATC | 1147 |
| Lys | Gly | Asp | Pro | Ile | Val | Gln | His | Arg | Pro | Met | Leu | Glu | Glu | Arg | Ile |      |
|     | 295 |     |     |     |     | 300 |     |     |     |     | 305 |     |     |     |     |      |
| GTG | GAG | CTG | TTC | AGA | AAC | TTA | ATG | AAA | AGT | GCC | TTT | GTG | GTG | GAG | CGG | 1195 |
| Val | Glu | Leu | Phe | Arg | Asn | Leu | Met | Lys | Ser | Ala | Phe | Val | Val | Glu | Arg |      |
| 310 |     |     |     |     | 315 |     |     |     |     | 320 |     |     |     |     | 325 |      |
| CAG | CCC | TGC | ATG | CCC | ATG | CAT | CCT | GAC | CGG | CCC | CTC | GTC | ATC | AAG | ACC | 1243 |
| Gln | Pro | Cys | Met | Pro | Met | His | Pro | Asp | Arg | Pro | Leu | Val | Ile | Lys | Thr |      |
|     |     |     |     | 330 |     |     |     |     | 335 |     |     |     |     | 340 |     |      |
| GGC | GTC | CAG | TTC | ACT | ACT | AAA | GTC | AGG | TTG | CTG | GTC | AAG | TTC | CCT | GAG | 1291 |
| Gly | Val | Gln | Phe | Thr | Thr | Lys | Val | Arg | Leu | Leu | Val | Lys | Phe | Pro | Glu |      |
|     |     |     | 345 |     |     |     |     |     | 350 |     |     |     |     | 355 |     |      |
| TTG | AAT | TAT | CAG | CTT | AAA | ATT | AAA | GTG | TGC | ATT | GAC | AAA | GAC | TCT | GGG | 1339 |
| Leu | Asn | Tyr | Gln | Leu | Lys | Ile | Lys | Val | Cys | Ile | Asp | Lys | Asp | Ser | Gly |      |
|     |     | 360 |     |     |     |     | 365 |     |     |     |     | 370 |     |     |     |      |
| GAC | GTT | GCA | GCT | CTC | AGA | GGA | TCC | CGG | AAA | TTT | AAC | ATT | CTG | GGC | ACA | 1387 |
| Asp | Val | Ala | Ala | Leu | Arg | Gly | Ser | Arg | Lys | Phe | Asn | Ile | Leu | Gly | Thr |      |
|     | 375 |     |     |     |     | 380 |     |     |     |     | 385 |     |     |     |     |      |
| AAC | ACA | AAA | GTG | ATG | AAC | ATG | GAA | GAA | TCC | AAC | AAC | GGC | AGC | CTC | TCT | 1435 |
| Asn | Thr | Lys | Val | Met | Asn | Met | Glu | Glu | Ser | Asn | Asn | Gly | Ser | Leu | Ser |      |
| 390 |     |     |     |     | 395 |     |     |     |     | 400 |     |     |     |     | 405 |      |
| GCA | GAA | TTC | AAA | CAC | TTG | ACC | CTG | AGG | GAG | CAG | AGA | TGT | GGG | AAT | GGG | 1483 |
| Ala | Glu | Phe | Lys | His | Leu | Thr | Leu | Arg | Glu | Gln | Arg | Cys | Gly | Asn | Gly |      |
|     |     |     |     | 410 |     |     |     |     | 415 |     |     |     |     | 420 |     |      |
| GGC | CGA | GCC | AAT | TGT | GAT | GCT | TCC | CTG | ATT | GTG | ACT | GAG | GAG | CTG | CAC | 1531 |
| Gly | Arg | Ala | Asn | Cys | Asp | Ala | Ser | Leu | Ile | Val | Thr | Glu | Glu | Leu | His |      |

|     |     |     |     | 425 |     |     |     | 430 |     |     |     | 435 |     |     |     |      |
|-----|-----|-----|-----|-----|-----|-----|-----|-----|-----|-----|-----|-----|-----|-----|-----|------|
| CTG | ATC | ACC | TTT | GAG | ACC | GAG | GTG | TAT | CAC | CAA | GGT | CTC | AAG | ATT | GAC | 1579 |
| Leu | Ile | Thr | Phe | Glu | Thr | Glu | Val | Tyr | His | Gln | Gly | Leu | Lys | Ile | Asp |      |
|     | 440 |     |     |     |     | 445 |     |     |     |     | 450 |     |     |     |     |      |

| CTA | GAG | ACC | CAC | TCC | TTG | TCA | GTT | GTG | GTG | ATC | TCC | AAC | ATC | TGT | CAG | 1627 |
| Leu | Glu | Thr | His | Ser | Leu | Ser | Val | Val | Val | Ile | Ser | Asn | Ile | Cys | Gln |
| 455 |     |     |     |     |     | 460 |     |     |     |     | 465 |     |     |     |     |

| ATG | CCA | AAT | GCC | TGG | GCG | TCC | ATC | CTG | TGG | TAC | AAC | ATG | CTG | ACC | AAC | 1675 |
| Met | Pro | Asn | Ala | Trp | Ala | Ser | Ile | Leu | Trp | Tyr | Asn | Met | Leu | Thr | Asn |
| 470 |     |     |     |     | 475 |     |     |     | 480 |     |     |     |     |     | 485 |

| AAT | CCC | AAG | AAT | GTG | AAC | TTC | TTC | ACT | AAG | CCG | CCA | ATT | GGA | ACC | TGG | 1723 |
| Asn | Pro | Lys | Asn | Val | Asn | Phe | Phe | Thr | Lys | Pro | Pro | Ile | Gly | Thr | Trp |
|     |     |     |     | 490 |     |     |     |     | 495 |     |     |     |     | 500 |     |

| GAC | CAA | GTG | GCC | GAG | GTG | CTC | AGC | TGG | CAG | TTC | TCG | TCC | ACC | ACC | AAG | 1771 |
| Asp | Gln | Val | Ala | Glu | Val | Leu | Ser | Trp | Gln | Phe | Ser | Ser | Thr | Thr | Lys |
|     |     |     | 505 |     |     |     |     | 510 |     |     |     |     | 515 |     |     |

| CGG | GGG | CTG | AGC | ATC | GAG | CAG | CTG | ACA | ACG | CTG | GCT | GAG | AAG | CTC | CTA | 1819 |
| Arg | Gly | Leu | Ser | Ile | Glu | Gln | Leu | Thr | Thr | Leu | Ala | Glu | Lys | Leu | Leu |
|     |     | 520 |     |     |     |     | 525 |     |     |     |     | 530 |     |     |     |

| GGG | CCT | GGT | GTG | AAC | TAC | TCA | GGG | TGT | CAG | ATC | ACA | TGG | GCT | AAC | TTC | 1867 |
| Gly | Pro | Gly | Val | Asn | Tyr | Ser | Gly | Cys | Gln | Ile | Thr | Trp | Ala | Asn | Phe |
| 535 |     |     |     |     | 540 |     |     |     |     | 545 |     |     |     |     |     |

| TGC | AAA | GAA | AAC | ATG | GCT | GGC | AAG | GGC | TTC | TCC | TAC | TGG | GTC | TGG | CTA | 1915 |
| Cys | Lys | Glu | Asn | Met | Ala | Gly | Lys | Gly | Phe | Ser | Tyr | Trp | Val | Trp | Leu |
| 550 |     |     |     |     | 555 |     |     |     |     | 560 |     |     |     |     | 565 |

| GAC | AAT | ATC | ATC | GAC | CTT | GTG | AAA | AAG | TAT | ATC | TTG | GCC | CTT | TGG | AAT | 1963 |
| Asp | Asn | Ile | Ile | Asp | Leu | Val | Lys | Lys | Tyr | Ile | Leu | Ala | Leu | Trp | Asn |
|     |     |     |     | 570 |     |     |     |     | 575 |     |     |     |     | 580 |     |

| GAA | GGG | TAC | ATC | ATG | GGT | TTC | ATC | AGC | AAG | GAG | CGG | GAG | CGG | GCC | ATC | 2011 |
| Glu | Gly | Tyr | Ile | Met | Gly | Phe | Ile | Ser | Lys | Glu | Arg | Glu | Arg | Ala | Ile |
|     |     |     | 585 |     |     |     |     | 590 |     |     |     |     | 595 |     |     |

| TTG | AGC | ACT | AAG | CCC | CCA | GGC | ACC | TTC | CTG | CTG | CGC | TTC | AGT | GAA | AGC | 2059 |
| Leu | Ser | Thr | Lys | Pro | Pro | Gly | Thr | Phe | Leu | Leu | Arg | Phe | Ser | Glu | Ser |
|     | 600 |     |     |     |     | 605 |     |     |     |     | 610 |     |     |     |     |

| AGC | AAA | GAA | GGA | GGC | GTC | ACT | TTC | ACT | TGG | GTG | GAG | AAG | GAC | ATC | AGC | 2107 |
| Ser | Lys | Glu | Gly | Gly | Val | Thr | Phe | Thr | Trp | Val | Glu | Lys | Asp | Ile | Ser |
| 615 |     |     |     |     | 620 |     |     |     |     | 625 |     |     |     |     |     |

| GGT | AAG | ACC | CAG | ATC | CAG | TCC | GTG | GAA | CCA | TAC | ACA | AAG | CAG | CAG | CTG | 2155 |
| Gly | Lys | Thr | Gln | Ile | Gln | Ser | Val | Glu | Pro | Tyr | Thr | Lys | Gln | Gln | Leu |
| 630 |     |     |     |     | 635 |     |     |     |     | 640 |     |     |     |     | 645 |

| AAC | AAC | ATG | TCA | TTT | GCT | GAA | ATC | ATC | ATG | GGC | TAT | AAG | ATC | ATG | GAT | 2203 |
| Asn | Asn | Met | Ser | Phe | Ala | Glu | Ile | Ile | Met | Gly | Tyr | Lys | Ile | Met | Asp |
|     |     |     |     | 650 |     |     |     |     | 655 |     |     |     |     | 660 |     |

| GCT | ACC | AAT | ATC | CTG | TTG | TCT | CCA | CTT | GTC | TAT | CTC | TAT | CCT | GAC | ATT | 2251 |
| Ala | Thr | Asn | Ile | Leu | Leu | Ser | Pro | Leu | Val | Tyr | Leu | Tyr | Pro | Asp | Ile |
|     |     |     | 665 |     |     |     |     | 670 |     |     |     |     | 675 |     |     |

| CCC | AAG | GAG | GAG | GCA | TTC | GGG | AAG | TAT | TGT | CGG | CCA | GAG | AGC | CAG | GAG | 2299 |
| Pro | Lys | Glu | Glu | Ala | Phe | Gly | Lys | Tyr | Cys | Arg | Pro | Glu | Ser | Gln | Glu |
|     |     | 680 |     |     |     |     | 685 |     |     |     |     | 690 |     |     |     |

| CAT | CCT | GAA | GCT | GAC | CCA | GGT | AGC | GCT | GCC | CCA | TAC | CTG | AAG | ACC | AAG | 2347 |
| His | Pro | Glu | Ala | Asp | Pro | Gly | Ser | Ala | Ala | Pro | Tyr | Leu | Lys | Thr | Lys |
|     | 695 |     |     |     |     | 700 |     |     |     |     | 705 |     |     |     |     |

| TTT | ATC | TGT | GTG | ACA | CCA | ACG | ACC | TGC | AGC | AAT | ACC | ATT | GAC | CTG | CCG | 2395 |
| Phe | Ile | Cys | Val | Thr | Pro | Thr | Thr | Cys | Ser | Asn | Thr | Ile | Asp | Leu | Pro |
| 710 |     |     |     |     | 715 |     |     |     |     | 720 |     |     |     |     | 725 |

| ATG | TCC | CCC | CGC | GCT | TTA | GAT | TCA | TTG | ATG | CAG | TTT | GGA | AAT | AAT | GGT | 2443 |
| Met | Ser | Pro | Arg | Ala | Leu | Asp | Ser | Leu | Met | Gln | Phe | Gly | Asn | Asn | Gly |
|     |     |     |     | 730 |     |     |     |     | 735 |     |     |     |     | 740 |     |

| GAA | GGT | GCT | GAA | CCC | TCA | GCA | GGA | GGG | CAG | TTT | GAG | TCC | CTC | ACC | TTT | 2491 |
| Glu | Gly | Ala | Glu | Pro | Ser | Ala | Gly | Gly | Gln | Phe | Glu | Ser | Leu | Thr | Phe |

|   |   |   |   |   | 745 |   |   |   | 750 |   |   |   |   | 755 |   |   |
|---|---|---|---|---|---|---|---|---|---|---|---|---|---|---|---|---|
| GAC | ATG | GAG | TTG | ACC | TCG | GAG | TGC | GCT | ACC | TCC | CCC | ATG | TGAGGAGCTG | | | 2540 |
| Asp | Met | Glu | Leu | Thr | Ser | Glu | Cys | Ala | Thr | Ser | Pro | Met | | | | |
|   |   | 760 |   |   |   |   | 765 |   |   |   |   | 770 |   |   |   |   |

```
AGAACGGAAG CTGCAGAAAG ATACGACTGA GGCGCCTACC TGCATTCTGC CACCCCTCAC      2600

ACAGCCAAAC CCCAGATCAT CTGAAACTAC TAACTTTGTG GTTCCAGATT TTTTTTAATC      2660

TCCTACTTCT GCTATCTTTG AGCAATCTGG GCACTTTTAA AAATAGAGAA ATGAGTGAAT      2720

GTGGGTGATC TGCTTTTATC TAAATGCAAA TAAGGATGTG TTCTCTGAGA CCCATGATCA      2780

GGGGATG                                                                2787
```

( 2 ) INFORMATION FOR SEQ ID NO:5:

( i ) SEQUENCE CHARACTERISTICS:
        ( A ) LENGTH: 770 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Ala Gln Trp Asn Gln Leu Gln Gln Leu Asp Thr Arg Tyr Leu Glu
 1               5                  10                  15

Gln Leu His Gln Leu Tyr Ser Asp Ser Phe Pro Met Glu Leu Arg Gln
              20                  25                  30

Phe Leu Ala Pro Trp Ile Glu Ser Gln Asp Trp Ala Tyr Ala Ala Ser
             35                  40                  45

Lys Glu Ser His Ala Thr Leu Val Phe His Asn Leu Leu Gly Glu Ile
     50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
             100                 105                 110

Ser Arg Leu Leu Gln Thr Ala Ala Thr Ala Ala Gln Gln Gly Gly Gln
         115                 120                 125

Ala Asn His Pro Thr Ala Ala Val Val Thr Glu Lys Gln Gln Met Leu
     130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                 165                 170                 175

Lys Thr Leu Lys Ser Gln Gly Asp Met Gln Asp Leu Asn Gly Asn Asn
             180                 185                 190

Gln Ser Val Thr Arg Gln Lys Met Gln Gln Leu Glu Gln Met Leu Thr
         195                 200                 205

Ala Leu Asp Gln Met Arg Arg Ser Ile Val Ser Glu Leu Ala Gly Leu
     210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                 245                 250                 255

Asn Ile Cys Leu Asp Arg Leu Glu Asn Trp Ile Thr Ser Leu Ala Glu
             260                 265                 270

Ser Gln Leu Gln Thr Arg Gln Gln Ile Lys Lys Leu Glu Glu Leu His
```

|     |     |     |     |     |     |     |     |     |     |     |     |     |     |
| --- | --- | --- | --- | --- | --- | --- | --- | --- | --- | --- | --- | --- | --- |
|     |     |     | 275 |     |     |     | 280 |     |     |     | 285 |     |     |
| Gln | Lys 290 | Val | Ser | Tyr | Lys | Gly 295 | Asp | Pro | Ile | Val | Gln 300 | His | Arg | Pro | Met |
| Leu 305 | Glu | Glu | Arg | Ile | Val 310 | Glu | Leu | Phe | Arg | Asn 315 | Leu | Met | Lys | Ser | Ala 320 |
| Phe | Val | Val | Glu | Arg 325 | Gln | Pro | Cys | Met | Pro 330 | Met | His | Pro | Asp | Arg 335 | Pro |
| Leu | Val | Ile | Lys 340 | Thr | Gly | Val | Gln | Phe 345 | Thr | Thr | Lys | Val | Arg 350 | Leu | Leu |
| Val | Lys | Phe 355 | Pro | Glu | Leu | Asn | Tyr 360 | Gln | Leu | Lys | Ile | Lys 365 | Val | Cys | Ile |
| Asp | Lys 370 | Asp | Ser | Gly | Asp | Val 375 | Ala | Ala | Leu | Arg | Gly 380 | Ser | Arg | Lys | Phe |
| Asn 385 | Ile | Leu | Gly | Thr | Asn 390 | Thr | Lys | Val | Met | Asn 395 | Met | Glu | Glu | Ser | Asn 400 |
| Asn | Gly | Ser | Leu | Ser 405 | Ala | Glu | Phe | Lys | His 410 | Leu | Thr | Leu | Arg | Glu 415 | Gln |
| Arg | Cys | Gly | Asn 420 | Gly | Gly | Arg | Ala | Asn 425 | Cys | Asp | Ala | Ser | Leu 430 | Ile | Val |
| Thr | Glu | Glu 435 | Leu | His | Leu | Ile | Thr 440 | Phe | Glu | Thr | Glu | Val 445 | Tyr | His | Gln |
| Gly | Leu 450 | Lys | Ile | Asp | Leu | Glu 455 | Thr | His | Ser | Leu | Ser 460 | Val | Val | Val | Ile |
| Ser 465 | Asn | Ile | Cys | Gln | Met 470 | Pro | Asn | Ala | Trp | Ala 475 | Ser | Ile | Leu | Trp | Tyr 480 |
| Asn | Met | Leu | Thr | Asn 485 | Asn | Pro | Lys | Asn | Val 490 | Asn | Phe | Phe | Thr | Lys 495 | Pro |
| Pro | Ile | Gly | Thr 500 | Trp | Asp | Gln | Val | Ala 505 | Glu | Val | Leu | Ser | Trp 510 | Gln | Phe |
| Ser | Ser | Thr 515 | Thr | Lys | Arg | Gly | Leu 520 | Ser | Ile | Glu | Gln | Leu 525 | Thr | Thr | Leu |
| Ala | Glu 530 | Lys | Leu | Leu | Gly | Pro 535 | Gly | Val | Asn | Tyr | Ser 540 | Gly | Cys | Gln | Ile |
| Thr 545 | Trp | Ala | Asn | Phe | Cys 550 | Lys | Glu | Asn | Met | Ala 555 | Gly | Lys | Gly | Phe | Ser 560 |
| Tyr | Trp | Val | Trp | Leu 565 | Asp | Asn | Ile | Ile | Asp 570 | Leu | Val | Lys | Lys | Tyr 575 | Ile |
| Leu | Ala | Leu | Trp 580 | Asn | Glu | Gly | Tyr | Ile 585 | Met | Gly | Phe | Ile | Ser 590 | Lys | Glu |
| Arg | Glu | Arg 595 | Ala | Ile | Leu | Ser | Thr 600 | Lys | Pro | Pro | Gly | Thr 605 | Phe | Leu | Leu |
| Arg | Phe 610 | Ser | Glu | Ser | Ser | Lys 615 | Glu | Gly | Gly | Val | Thr 620 | Phe | Thr | Trp | Val |
| Glu 625 | Lys | Asp | Ile | Ser | Gly 630 | Lys | Thr | Gln | Ile | Gln 635 | Ser | Val | Glu | Pro | Tyr 640 |
| Thr | Lys | Gln | Gln | Leu 645 | Asn | Asn | Met | Ser | Phe 650 | Ala | Glu | Ile | Ile | Met 655 | Gly |
| Tyr | Lys | Ile | Met 660 | Asp | Ala | Thr | Asn | Ile 665 | Leu | Leu | Ser | Pro | Leu 670 | Val | Tyr |
| Leu | Tyr | Pro 675 | Asp | Ile | Pro | Lys | Glu 680 | Glu | Ala | Phe | Gly | Lys 685 | Tyr | Cys | Arg |
| Pro | Glu 690 | Ser | Gln | Glu | His | Pro 695 | Glu | Ala | Asp | Pro | Gly 700 | Ser | Ala | Ala | Pro |

| | | | | | | | | | | | | | | |
|---|---|---|---|---|---|---|---|---|---|---|---|---|---|---|
| Tyr | Leu | Lys | Thr | Lys | Phe | Ile | Cys | Val | Thr | Pro | Thr | Thr | Cys | Ser | Asn |
| 705 | | | | | 710 | | | | | 715 | | | | | 720 |
| Thr | Ile | Asp | Leu | Pro | Met | Ser | Pro | Arg | Ala | Leu | Asp | Ser | Leu | Met | Gln |
| | | | | 725 | | | | | 730 | | | | | 735 | |
| Phe | Gly | Asn | Asn | Gly | Glu | Gly | Ala | Glu | Pro | Ser | Ala | Gly | Gly | Gln | Phe |
| | | | 740 | | | | | 745 | | | | | 750 | | |
| Glu | Ser | Leu | Thr | Phe | Asp | Met | Glu | Leu | Thr | Ser | Glu | Cys | Ala | Thr | Ser |
| | | 755 | | | | | 760 | | | | | 765 | | | |
| Pro | Met | | | | | | | | | | | | | | |
| | 770 | | | | | | | | | | | | | | |

( 2 ) INFORMATION FOR SEQ ID NO:6:

( i ) SEQUENCE CHARACTERISTICS:
        ( A ) LENGTH: 2310 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:6:

| | | | | | |
|---|---|---|---|---|---|
| ATGGCTCAGT | GGAACCAGCT | GCAGCAGCTG | GACACACGCT | ACCTGGAGCA | GCTGCACCAG | 60 |
| CTGTACAGCG | ACAGCTTCCC | CATGGAGCTG | CGGCAGTTCC | TGGCACCTTG | GATTGAGAGT | 120 |
| CAAGACTGGG | CATATGCAGC | CAGCAAAGAG | TCACATGCCA | CGTTGGTGTT | TCATAATCTC | 180 |
| TTGGGTGAAA | TTGACCAGCA | ATATAGCCGA | TTCCTGCAAG | AGTCCAATGT | CCTCTATCAG | 240 |
| CACAACCTTC | GAAGAATCAA | GCAGTTTCTG | CAGAGCAGGT | ATCTTGAGAA | GCCAATGGAA | 300 |
| ATTGCCCGGA | TCGTGGCCCG | ATGCCTGTGG | GAAGAGTCTC | GCCTCCTCCA | GACGGCAGCC | 360 |
| ACGGCAGCCC | AGCAAGGGGG | CCAGGCCAAC | CACCCAACAG | CTGCCGTAGT | GACAGAGAAG | 420 |
| CAGCAGATGT | GGAGCAGCA | TCTTCAGGAT | GTCCGGAAGC | GAGTGCAGGA | TCTAGAACAG | 480 |
| AAAATGAAGG | TGGTGGAGAA | CCTCCAGGAC | GACTTTGATT | TCAACTACAA | AACCCTCAAG | 540 |
| AGCCAAGGAG | ACATGCAGGA | TCTGAATGGA | ACAACCAGT | CTGTGACCAG | ACAGAAGATG | 600 |
| CAGCAGCTGG | AACAGATGCT | CACAGCCCTG | GACCAGATGC | GGAGAAGCAT | TGTGAGTGAG | 660 |
| CTGGCGGGGC | TCTTGTCAGC | AATGGAGTAC | GTGCAGAAGA | CACTGACTGA | TGAAGAGCTG | 720 |
| GCTGACTGGA | AGAGGCGGCA | GCAGATCGCG | TGCATCGGAG | CCCTCCCAA | CATCTGCCTG | 780 |
| GACCGTCTGG | AAAACTGGAT | AACTTCATTA | GCAGAATCTC | AACTTCAGAC | CCGCCAACAA | 840 |
| ATTAAGAAAC | TGGAGGAGCT | GCAGCAGAAA | GTGTCCTACA | AGGGCGACCC | TATCGTGCAG | 900 |
| CACCGGCCCA | TGCTGGAGGA | GAGGATCGTG | GAGCTGTTCA | GAAACTTAAT | GAAGAGTGCC | 960 |
| TTCGTGGTGG | AGCGGCAGCC | CTGCATGCCC | ATGCACCCGG | ACCGGCCCTT | AGTCATCAAG | 1020 |
| ACTGGTGTCC | AGTTTACCAC | GAAAGTCAGG | TTGCTGGTCA | AATTTCCTGA | GTTGAATTAT | 1080 |
| CAGCTTAAAA | TTAAAGTGTG | CATTGATAAA | GACTCTGGCG | ATGTTGCTGC | CCTCAGAGGG | 1140 |
| TCTCGGAAAT | TTAACATTCT | GGGCACGAAC | ACAAAAGTGA | TTAACATGGA | GGAGTCTAAC | 1200 |
| AACGGCAGCC | TGTCTGCAGA | GTTCAAGCAC | CTGACCCTTA | GGGAGCAGAG | ATGTGGGAAT | 1260 |
| GGAGGCCGTG | CCAATTGTGA | TGCCTCCTTG | ATCGTGACTG | AGGAGCTGCA | CCTGATCACC | 1320 |
| TTCGAGACTG | AGGTGTACCA | CCAAGGCCTC | AAGATTGACC | TAGAGACCCA | CTCCTTGCCA | 1380 |
| GTTGTGGTGA | TCTCCAACAT | CTGTCAGATG | CCAAATGCTT | GGGCATCAAT | CCTGTGGTAT | 1440 |
| AACATGCTGA | CCAATAACCC | CAAGAACGTG | AACTTCTTCA | CTAAGCCGCC | AATTGGAACC | 1500 |
| TGGGACCAAG | TGGCCGAGGT | GCTCAGCTGG | CAGTTCTCGT | CCACCACCAA | GCGGGGGCTG | 1560 |

| | | | | | |
|---|---|---|---|---|---|
| AGCATCGAGC | AGCTGACAAC | GCTGGCTGAG | AAGCTCCTAG | GGCCTGGTGT | GAACTACTCA | 1620 |
| GGGTGTCAGA | TCACATGGGC | TAAATTCTGC | AAAGAAAACA | TGGCTGGCAA | GGGCTTCTCC | 1680 |
| TTCTGGGTCT | GGCTAGACAA | TATCATCGAC | CTTGTGAAAA | AGTATATCTT | GGCCCTTTGG | 1740 |
| AATGAAGGGT | ACATCATGGG | TTTCATCAGC | AAGGAGCGGG | AGCGGGCCAT | CCTAAGCACA | 1800 |
| AAGCCCCCGG | GCACCTTCCT | ACTGCGCTTC | AGCGAGAGCA | GCAAAGAAGG | AGGGGTCACT | 1860 |
| TTCACTTGGG | TGGAAAAGGA | CATCAGTGGC | AAGACCCAGA | TCCAGTCTGT | AGAGCCATAC | 1920 |
| ACCAAGCAGC | AGCTGAACAA | CATGTCATTT | GCTGAAATCA | TCATGGGCTA | TAAGATCATG | 1980 |
| GATGCGACCA | ACATCCTGGT | GTCTCCACTT | GTCTACCTCT | ACCCCGACAT | TCCCAAGGAG | 2040 |
| GAGGCATTTG | GAAAGTACTG | TAGGCCCGAG | AGCCAGGAGC | ACCCCGAAGC | CGACCCAGGT | 2100 |
| AGTGCTGCCC | CGTACCTGAA | GACCAAGTTC | ATCTGTGTGA | CACCAACGAC | CTGCAGCAAT | 2160 |
| ACCATTGACC | TGCCGATGTC | CCCCCGCACT | TTAGATTCAT | TGATGCAGTT | TGGAAATAAC | 2220 |
| GGTGAAGGTG | CTGAGCCCTC | AGCAGGAGGG | CAGTTTGAGT | CGCTCACGTT | TGACATGGAT | 2280 |
| CTGACCTCGG | AGTGTGCTAC | CTCCCCCATG | | | | 2310 |

( 2 ) INFORMATION FOR SEQ ID NO:7:

( i ) SEQUENCE CHARACTERISTICS:
( A ) LENGTH: 2652 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:7:

| | | | | | |
|---|---|---|---|---|---|
| CTGGAGGGGC | TGTAATTCAG | CGGTTTCCGG | AGCTGCAGTG | TAGACAGGGA | GGGGGAACCT | 60 |
| GGGGTTCCGA | CGTCGCGGCG | GAGGGAACGA | GCCCTAACCG | GATCGCTGAG | GTACAACCCC | 120 |
| GCTCGGTGTC | GCCTGACCGC | GTCGGCTAGG | AGAGGCCAGG | CGGCCCTCGG | GAGCCCAGCA | 180 |
| GCTCGCGCCT | GGAGTCAGCG | CAGGCCGGCC | AGTCGGGCCT | CAGCCCCGGA | GACAGTCGAG | 240 |
| ACCCCTGACT | GCAGCAGGAT | GGCTCAGTGG | AACCAGCTGC | AGCAGCTGGA | CACACGCTAC | 300 |
| CTGGAGCAGC | TGCACCAGCT | GTACAGCGAC | AGCTTCCCCA | TGGAGCTGCG | GCAGTTCCTG | 360 |
| GCACCTTGGA | TTGAGAGTCA | AGACTGGGCA | TATGCAGCCA | GCAAAGAGTC | ACATGCCACG | 420 |
| TTGGTGTTTC | ATAATCTCTT | GGGTGAAATT | GACCAGCAAT | ATAGCCGATT | CCTGCAAGAG | 480 |
| TCCAATGTCC | TCTATCAGCA | CAACCTTCGA | AGAATCAAGC | AGTTTCTGCA | GAGCAGGTAT | 540 |
| CTTGAGAAGC | CAATGGAAAT | TGCCCGGATC | GTGGCCCGAT | GCCTGTGGGA | AGAGTCTCGC | 600 |
| CTCCTCCAGA | CGGCAGCCAC | GGCAGCCCAG | CAAGGGGCC | AGGCCAACCA | CCCAACAGCT | 660 |
| GCCGTAGTGA | CAGAGAAGCA | GCAGATGTTG | GAGCAGCATC | TTCAGGATGT | CCGGAAGCGA | 720 |
| GTGCAGGATC | TAGAACAGAA | AATGAAGGTG | GTGGAGAACC | TCCAGGACGA | CTTTGATTTC | 780 |
| AACTACAAAA | CCCTCAAGAG | CCAAGGAGAC | ATGCAGGATC | TGAATGGAAA | CAACCAGTCT | 840 |
| GTGACCAGAC | AGAAGATGCA | GCAGCTGGAA | CAGATGCTCA | CAGCCCTGGA | CCAGATGCGG | 900 |
| AGAAGCATTG | TGAGTGAGCT | GGCGGGGCTC | TTGTCAGCAA | TGGAGTACGT | GCAGAAGACA | 960 |
| CTGACTGATG | AAGAGCTGGC | TGACTGGAAG | AGGCGGCAGC | AGATCGCGTG | CATCGGAGGC | 1020 |
| CCTCCCAACA | TCTGCCTGGA | CCGTCTGGAA | AACTGGATAA | CTTCATTAGC | AGAATCTCAA | 1080 |
| CTTCAGACCC | GCCAACAAAT | TAAGAAACTG | GAGGAGCTGC | AGCAGAAAGT | GTCCTACAAG | 1140 |
| GGCGACCCTA | TCGTGCAGCA | CCGGCCCATG | CTGGAGGAGA | GGATCGTGGA | GCTGTTCAGA | 1200 |
| AACTTAATGA | AGAGTGCCTT | CGTGGTGGAG | CGGCAGCCCT | GCATGCCCAT | GCACCCGGAC | 1260 |

-continued

| | | | | | |
|---|---|---|---|---|---|
| CGGCCCTTAG | TCATCAAGAC | TGGTGTCCAG | TTTACCACGA | AAGTCAGGTT | GCTGGTCAAA | 1320 |
| TTTCCTGAGT | TGAATTATCA | GCTTAAAATT | AAAGTGTGCA | TTGATAAAGA | CTCTGGCGAT | 1380 |
| GTTGCTGCCC | TCAGAGGGTC | TCGGAAATTT | AACATTCTGG | GCACGAACAC | AAAAGTGATT | 1440 |
| AACATGGAGG | AGTCTAACAA | CGGCAGCCTG | TCTGCAGAGT | TCAAGCACCT | GACCCTTAGG | 1500 |
| GAGCAGAGAT | GTGGGAATGG | AGGCCGTGCC | AATTGTGATG | CCTCCTTGAT | CGTGACTGAG | 1560 |
| GAGCTGCACC | TGATCACCTT | CGAGACTGAG | GTGTACCACC | AAGGCCTCAA | GATTGACCTA | 1620 |
| GAGACCCACT | CCTTGCCAGT | TGTGGTGATC | TCCAACATCT | GTCAGATGCC | AAATGCTTGG | 1680 |
| GCATCAATCC | TGTGGTATAA | CATGCTGACC | AATAACCCCA | GAACGTGAA | CTTCTTCACT | 1740 |
| AAGCCGCCAA | TTGGAACCTG | GGACCAAGTG | GCCGAGGTGC | TCAGCTGGCA | GTTCTCGTCC | 1800 |
| ACCACCAAGC | GGGGGCTGAG | CATCGAGCAG | CTGACAACGC | TGGCTGAGAA | GCTCCTAGGG | 1860 |
| CCTGGTGTGA | ACTACTCAGG | GTGTCAGATC | ACATGGGCTA | AATTCTGCAA | AGAAAACATG | 1920 |
| GCTGGCAAGG | GCTTCTCCTT | CTGGGTCTGG | CTAGACAATA | TCATCGACCT | TGTGAAAAAG | 1980 |
| TATATCTTGG | CCCTTTGGAA | TGAAGGGTAC | ATCATGGGTT | TCATCAGCAA | GGAGCGGGAG | 2040 |
| CGGGCCATCC | TAAGCACAAA | GCCCCCGGGC | ACCTTCCTAC | TGCGCTTCAG | CGAGAGCAGC | 2100 |
| AAAGAAGGAG | GGGTCACTTT | CACTTGGGTG | GAAAAGGACA | TCAGTGGCAA | GACCCAGATC | 2160 |
| CAGTCTGTAG | AGCCATACAC | CAAGCAGCAG | CTGAACAACA | TGTCATTTGC | TGAAATCATC | 2220 |
| ATGGGCTATA | AGATCATGGA | TGCGACCAAC | ATCCTGGTGT | CTCCACTTGT | CTACCTCTAC | 2280 |
| CCCGACATTC | CAAGGAGGA | GGCATTTGGA | AAGTACTGTA | GGCCCGAGAG | CCAGGAGCAC | 2340 |
| CCCGAAGCCG | ACCCAGGTAG | TGCTGCCCCG | TACCTGAAGA | CCAAGTTCAT | CTGTGTGACA | 2400 |
| CCAACGACCT | GCAGCAATAC | CATTGACCTG | CCGATGTCCC | CCCGCACTTT | AGATTCATTG | 2460 |
| ATGCAGTTTG | GAAATAACGG | TGAAGGTGCT | GAGCCCTCAG | CAGGAGGGCA | GTTTGAGTCG | 2520 |
| CTCACGTTTG | ACATGGATCT | GACCTCGGAG | TGTGCTACCT | CCCCATGTG | AGGAGCTGAA | 2580 |
| ACCAGAAGCT | GCAGAGACGT | GACTTGAGAC | ACCTGCCCCG | TGCTCCACCC | CTAAGCAGCC | 2640 |
| GAACCCCATA | TC | | | | | 2652 |

( 2 ) INFORMATION FOR SEQ ID NO:8:

( i ) SEQUENCE CHARACTERISTICS:
      ( A ) LENGTH: 2652 base pairs
      ( B ) TYPE: nucleic acid
      ( C ) STRANDEDNESS: single
      ( D ) TOPOLOGY: linear ( i i ) MOLECULE TYPE: cDNA to mRNA ( v i ) ORIGINAL SOURCE:
      ( A ) ORGANISM: Mouse
      ( F ) TISSUE TYPE: Liver ( i x ) FEATURE:
      ( A ) NAME/KEY: CDS
      ( B ) LOCATION: 259..2568

( x i ) SEQUENCE DESCRIPTION: SEQ ID NO:8:

| | | | | | |
|---|---|---|---|---|---|
| CTGGAGGGGC | TGTAATTCAG | CGGTTTCCGG | AGCTGCAGTG | TAGACAGGGA | GGGGAACCT | 60 |
| GGGGTTCCGA | CGTCGCGGCG | GAGGGAACGA | GCCCTAACCG | GATCGCTGAG | GTACAACCCC | 120 |
| GCTCGGTGTC | GCCTGACCGC | GTCGGCTAGG | AGAGGCCAGG | CGGCCCTCGG | GAGCCCAGCA | 180 |
| GCTCGCGCCT | GGAGTCAGCG | CAGGCCGGCC | AGTCGGGCCT | CAGCCCCGGA | GACAGTCGAG | 240 |
| ACCCCTGACT | GCAGCAGG | ATG GCT CAG TGG AAC CAG CTG CAG CAG CTG GAC | | | | 291 |
| | | Met Ala Gln Trp Asn Gln Leu Gln Gln Leu Asp | | | | |

-continued

|   |   |   |   | 1 |   |   |   |   | 5 |   |   |   |   | 10 |   |   |   |
|---|---|---|---|---|---|---|---|---|---|---|---|---|---|---|---|---|---|

| ACA | CGC | TAC | CTG | GAG | CAG | CTG | CAC | CAG | CTG | TAC | AGC | GAC | AGC | TTC | CCC | 339 |
| Thr | Arg | Tyr | Leu | Glu | Gln | Leu | His | Gln | Leu | Tyr | Ser | Asp | Ser | Phe | Pro | |
|     |     |     |     | 15  |     |     |     | 20  |     |     |     |     | 25  |     |     | |

| ATG | GAG | CTG | CGG | CAG | TTC | CTG | GCA | CCT | TGG | ATT | GAG | AGT | CAA | GAC | TGG | 387 |
| Met | Glu | Leu | Arg | Gln | Phe | Leu | Ala | Pro | Trp | Ile | Glu | Ser | Gln | Asp | Trp | |
|     |     | 30  |     |     |     |     | 35  |     |     |     |     | 40  |     |     |     | |

| GCA | TAT | GCA | GCC | AGC | AAA | GAG | TCA | CAT | GCC | ACG | TTG | GTG | TTT | CAT | AAT | 435 |
| Ala | Tyr | Ala | Ala | Ser | Lys | Glu | Ser | His | Ala | Thr | Leu | Val | Phe | His | Asn | |
|     |     | 45  |     |     |     | 50  |     |     |     |     | 55  |     |     |     |     | |

| CTC | TTG | GGT | GAA | ATT | GAC | CAG | CAA | TAT | AGC | CGA | TTC | CTG | CAA | GAG | TCC | 483 |
| Leu | Leu | Gly | Glu | Ile | Asp | Gln | Gln | Tyr | Ser | Arg | Phe | Leu | Gln | Glu | Ser | |
| 60  |     |     |     |     | 65  |     |     |     |     | 70  |     |     |     |     | 75  | |

| AAT | GTC | CTC | TAT | CAG | CAC | AAC | CTT | CGA | AGA | ATC | AAG | CAG | TTT | CTG | CAG | 531 |
| Asn | Val | Leu | Tyr | Gln | His | Asn | Leu | Arg | Arg | Ile | Lys | Gln | Phe | Leu | Gln | |
|     |     |     |     | 80  |     |     |     |     | 85  |     |     |     |     | 90  |     | |

| AGC | AGG | TAT | CTT | GAG | AAG | CCA | ATG | GAA | ATT | GCC | CGG | ATC | GTG | GCC | CGA | 579 |
| Ser | Arg | Tyr | Leu | Glu | Lys | Pro | Met | Glu | Ile | Ala | Arg | Ile | Val | Ala | Arg | |
|     |     |     | 95  |     |     |     |     | 100 |     |     |     |     | 105 |     |     | |

| TGC | CTG | TGG | GAA | GAG | TCT | CGC | CTC | CTC | CAG | ACG | GCA | GCC | ACG | GCA | GCC | 627 |
| Cys | Leu | Trp | Glu | Glu | Ser | Arg | Leu | Leu | Gln | Thr | Ala | Ala | Thr | Ala | Ala | |
|     |     |     | 110 |     |     |     |     | 115 |     |     |     |     | 120 |     |     | |

| CAG | CAA | GGG | GGC | CAG | GCC | AAC | CAC | CCA | ACA | GCT | GCC | GTA | GTG | ACA | GAG | 675 |
| Gln | Gln | Gly | Gly | Gln | Ala | Asn | His | Pro | Thr | Ala | Ala | Val | Val | Thr | Glu | |
|     |     | 125 |     |     |     |     | 130 |     |     |     |     | 135 |     |     |     | |

| AAG | CAG | CAG | ATG | TTG | GAG | CAG | CAT | CTT | CAG | GAT | GTC | CGG | AAG | CGA | GTG | 723 |
| Lys | Gln | Gln | Met | Leu | Glu | Gln | His | Leu | Gln | Asp | Val | Arg | Lys | Arg | Val | |
| 140 |     |     |     |     | 145 |     |     |     |     | 150 |     |     |     |     | 155 | |

| CAG | GAT | CTA | GAA | CAG | AAA | ATG | AAG | GTG | GTG | GAG | AAC | CTC | CAG | GAC | GAC | 771 |
| Gln | Asp | Leu | Glu | Gln | Lys | Met | Lys | Val | Val | Glu | Asn | Leu | Gln | Asp | Asp | |
|     |     |     |     | 160 |     |     |     |     | 165 |     |     |     |     | 170 |     | |

| TTT | GAT | TTC | AAC | TAC | AAA | ACC | CTC | AAG | AGC | CAA | GGA | GAC | ATG | CAG | GAT | 819 |
| Phe | Asp | Phe | Asn | Tyr | Lys | Thr | Leu | Lys | Ser | Gln | Gly | Asp | Met | Gln | Asp | |
|     |     |     | 175 |     |     |     |     | 180 |     |     |     |     | 185 |     |     | |

| CTG | AAT | GGA | AAC | AAC | CAG | TCT | GTG | ACC | AGA | CAG | AAG | ATG | CAG | CAG | CTG | 867 |
| Leu | Asn | Gly | Asn | Asn | Gln | Ser | Val | Thr | Arg | Gln | Lys | Met | Gln | Gln | Leu | |
|     |     |     | 190 |     |     |     |     | 195 |     |     |     |     | 200 |     |     | |

| GAA | CAG | ATG | CTC | ACA | GCC | CTG | GAC | CAG | ATG | CGG | AGA | AGC | ATT | GTG | AGT | 915 |
| Glu | Gln | Met | Leu | Thr | Ala | Leu | Asp | Gln | Met | Arg | Arg | Ser | Ile | Val | Ser | |
|     |     |     | 205 |     |     |     |     | 210 |     |     |     |     | 215 |     |     | |

| GAG | CTG | GCG | GGG | CTC | TTG | TCA | GCA | ATG | GAG | TAC | GTG | CAG | AAG | ACA | CTG | 963 |
| Glu | Leu | Ala | Gly | Leu | Leu | Ser | Ala | Met | Glu | Tyr | Val | Gln | Lys | Thr | Leu | |
| 220 |     |     |     |     | 225 |     |     |     |     | 230 |     |     |     |     | 235 | |

| ACT | GAT | GAA | GAG | CTG | GCT | GAC | TGG | AAG | AGG | CGG | CAG | CAG | ATC | GCG | TGC | 1011 |
| Thr | Asp | Glu | Glu | Leu | Ala | Asp | Trp | Lys | Arg | Arg | Gln | Gln | Ile | Ala | Cys | |
|     |     |     |     | 240 |     |     |     |     | 245 |     |     |     |     | 250 |     | |

| ATC | GGA | GGC | CCT | CCC | AAC | ATC | TGC | CTG | GAC | CGT | CTG | GAA | AAC | TGG | ATA | 1059 |
| Ile | Gly | Gly | Pro | Pro | Asn | Ile | Cys | Leu | Asp | Arg | Leu | Glu | Asn | Trp | Ile | |
|     |     |     |     | 255 |     |     |     |     | 260 |     |     |     |     | 265 |     | |

| ACT | TCA | TTA | GCA | GAA | TCT | CAA | CTT | CAG | ACC | CGC | CAA | CAA | ATT | AAG | AAA | 1107 |
| Thr | Ser | Leu | Ala | Glu | Ser | Gln | Leu | Gln | Thr | Arg | Gln | Gln | Ile | Lys | Lys | |
|     |     | 270 |     |     |     |     | 275 |     |     |     |     | 280 |     |     |     | |

| CTG | GAG | GAG | CTG | CAG | CAG | AAA | GTG | TCC | TAC | AAG | GGC | GAC | CCT | ATC | GTG | 1155 |
| Leu | Glu | Glu | Leu | Gln | Gln | Lys | Val | Ser | Tyr | Lys | Gly | Asp | Pro | Ile | Val | |
|     | 285 |     |     |     |     | 290 |     |     |     |     | 295 |     |     |     |     | |

| CAG | CAC | CGG | CCC | ATG | CTG | GAG | GAG | AGG | ATC | GTG | GAG | CTG | TTC | AGA | AAC | 1203 |
| Gln | His | Arg | Pro | Met | Leu | Glu | Glu | Arg | Ile | Val | Glu | Leu | Phe | Arg | Asn | |
| 300 |     |     |     |     | 305 |     |     |     |     | 310 |     |     |     |     | 315 | |

| TTA | ATG | AAG | AGT | GCC | TTC | GTG | GTG | GAG | CGG | CAG | CCC | TGC | ATG | CCC | ATG | 1251 |
| Leu | Met | Lys | Ser | Ala | Phe | Val | Val | Glu | Arg | Gln | Pro | Cys | Met | Pro | Met | |

|  |  |  |  |  |  |  |  |  |  |  |  |  |  |  |  |
|---|---|---|---|---|---|---|---|---|---|---|---|---|---|---|---|
|  |  |  |  |  | 320 |  |  |  |  | 325 |  |  |  |  | 330 |

```
CAC  CCG  GAC  CGG  CCC  TTA  GTC  ATC  AAG  ACT  GGT  GTC  CAG  TTT  ACC  ACG       1299
His  Pro  Asp  Arg  Pro  Leu  Val  Ile  Lys  Thr  Gly  Val  Gln  Phe  Thr  Thr
               335                 340                      345

AAA  GTC  AGG  TTG  CTG  GTC  AAA  TTT  CCT  GAG  TTG  AAT  TAT  CAG  CTT  AAA       1347
Lys  Val  Arg  Leu  Leu  Val  Lys  Phe  Pro  Glu  Leu  Asn  Tyr  Gln  Leu  Lys
               350                 355                      360

ATT  AAA  GTG  TGC  ATT  GAT  AAA  GAC  TCT  GGC  GAT  GTT  GCT  GCC  CTC  AGA       1395
Ile  Lys  Val  Cys  Ile  Asp  Lys  Asp  Ser  Gly  Asp  Val  Ala  Ala  Leu  Arg
               365                 370                      375

GGG  TCT  CGG  AAA  TTT  AAC  ATT  CTG  GGC  ACG  AAC  ACA  AAA  GTG  ATT  AAC       1443
Gly  Ser  Arg  Lys  Phe  Asn  Ile  Leu  Gly  Thr  Asn  Thr  Lys  Val  Ile  Asn
380                      385                 390                      395

ATG  GAG  GAG  TCT  AAC  AAC  GGC  AGC  CTG  TCT  GCA  GAG  TTC  AAG  CAC  CTG       1491
Met  Glu  Glu  Ser  Asn  Asn  Gly  Ser  Leu  Ser  Ala  Glu  Phe  Lys  His  Leu
                    400                      405                      410

ACC  CTT  AGG  GAG  CAG  AGA  TGT  GGG  AAT  GGA  GGC  CGT  GCC  AAT  TGT  GAT       1539
Thr  Leu  Arg  Glu  Gln  Arg  Cys  Gly  Asn  Gly  Gly  Arg  Ala  Asn  Cys  Asp
               415                 420                      425

GCC  TCC  TTG  ATC  GTG  ACT  GAG  GAG  CTG  CAC  CTG  ATC  ACC  TTC  GAG  ACT       1587
Ala  Ser  Leu  Ile  Val  Thr  Glu  Glu  Leu  His  Leu  Ile  Thr  Phe  Glu  Thr
          430                      435                      440

GAG  GTG  TAC  CAC  CAA  GGC  CTC  AAG  ATT  GAC  CTA  GAG  ACC  CAC  TCC  TTG       1635
Glu  Val  Tyr  His  Gln  Gly  Leu  Lys  Ile  Asp  Leu  Glu  Thr  His  Ser  Leu
          445                      450                      455

CCA  GTT  GTG  GTG  ATC  TCC  AAC  ATC  TGT  CAG  ATG  CCA  AAT  GCT  TGG  GCA       1683
Pro  Val  Val  Val  Ile  Ser  Asn  Ile  Cys  Gln  Met  Pro  Asn  Ala  Trp  Ala
460                      465                 470                      475

TCA  ATC  CTG  TGG  TAT  AAC  ATG  CTG  ACC  AAT  AAC  CCC  AAG  AAC  GTG  AAC       1731
Ser  Ile  Leu  Trp  Tyr  Asn  Met  Leu  Thr  Asn  Asn  Pro  Lys  Asn  Val  Asn
                    480                      485                      490

TTC  TTC  ACT  AAG  CCG  CCA  ATT  GGA  ACC  TGG  GAC  CAA  GTG  GCC  GAG  GTG       1779
Phe  Phe  Thr  Lys  Pro  Pro  Ile  Gly  Thr  Trp  Asp  Gln  Val  Ala  Glu  Val
               495                      500                 505

CTC  AGC  TGG  CAG  TTC  TCG  TCC  ACC  ACC  AAG  CGG  GGG  CTG  AGC  ATC  GAG       1827
Leu  Ser  Trp  Gln  Phe  Ser  Ser  Thr  Thr  Lys  Arg  Gly  Leu  Ser  Ile  Glu
          510                      515                      520

CAG  CTG  ACA  ACG  CTG  GCT  GAG  AAG  CTC  CTA  GGG  CCT  GGT  GTG  AAC  TAC       1875
Gln  Leu  Thr  Thr  Leu  Ala  Glu  Lys  Leu  Leu  Gly  Pro  Gly  Val  Asn  Tyr
     525                      530                      535

TCA  GGG  TGT  CAG  ATC  ACA  TGG  GCT  AAA  TTC  TGC  AAA  GAA  AAC  ATG  GCT       1923
Ser  Gly  Cys  Gln  Ile  Thr  Trp  Ala  Lys  Phe  Cys  Lys  Glu  Asn  Met  Ala
540                      545                 550                      555

GGC  AAG  GGC  TTC  TCC  TTC  TGG  GTC  TGG  CTA  GAC  AAT  ATC  ATC  GAC  CTT       1971
Gly  Lys  Gly  Phe  Ser  Phe  Trp  Val  Trp  Leu  Asp  Asn  Ile  Ile  Asp  Leu
                    560                      565                      570

GTG  AAA  AAG  TAT  ATC  TTG  GCC  CTT  TGG  AAT  GAA  GGG  TAC  ATC  ATG  GGT       2019
Val  Lys  Lys  Tyr  Ile  Leu  Ala  Leu  Trp  Asn  Glu  Gly  Tyr  Ile  Met  Gly
               575                      580                 585

TTC  ATC  AGC  AAG  GAG  CGG  GAG  CGG  GCC  ATC  CTA  AGC  ACA  AAG  CCC  CCG       2067
Phe  Ile  Ser  Lys  Glu  Arg  Glu  Arg  Ala  Ile  Leu  Ser  Thr  Lys  Pro  Pro
          590                      595                      600

GGC  ACC  TTC  CTA  CTG  CGC  TTC  AGC  GAG  AGC  AGC  AAA  GAA  GGA  GGG  GTC       2115
Gly  Thr  Phe  Leu  Leu  Arg  Phe  Ser  Glu  Ser  Ser  Lys  Glu  Gly  Gly  Val
          605                      610                      615

ACT  TTC  ACT  TGG  GTG  GAA  AAG  GAC  ATC  AGT  GGC  AAG  ACC  CAG  ATC  CAG       2163
Thr  Phe  Thr  Trp  Val  Glu  Lys  Asp  Ile  Ser  Gly  Lys  Thr  Gln  Ile  Gln
620                      625                 630                      635

TCT  GTA  GAG  CCA  TAC  ACC  AAG  CAG  CAG  CTG  AAC  AAC  ATG  TCA  TTT  GCT       2211
Ser  Val  Glu  Pro  Tyr  Thr  Lys  Gln  Gln  Leu  Asn  Asn  Met  Ser  Phe  Ala
```

|     |     |     |     |     | 640 |     |     |     | 645 |     |     |     | 650 |     |     |      |
| --- | --- | --- | --- | --- | --- | --- | --- | --- | --- | --- | --- | --- | --- | --- | --- | ---- |
| GAA | ATC | ATC | ATG | GGC | TAT | AAG | ATC | ATG | GAT | GCG | ACC | AAC | ATC | CTG | GTG | 2259 |
| Glu | Ile | Ile | Met | Gly | Tyr | Lys | Ile | Met | Asp | Ala | Thr | Asn | Ile | Leu | Val |      |
|     |     |     | 655 |     |     |     | 660 |     |     |     |     |     | 665 |     |     |      |
| TCT | CCA | CTT | GTC | TAC | CTC | TAC | CCC | GAC | ATT | CCC | AAG | GAG | GAG | GCA | TTT | 2307 |
| Ser | Pro | Leu | Val | Tyr | Leu | Tyr | Pro | Asp | Ile | Pro | Lys | Glu | Glu | Ala | Phe |      |
|     |     | 670 |     |     |     | 675 |     |     |     |     | 680 |     |     |     |     |      |
| GGA | AAG | TAC | TGT | AGG | CCC | GAG | AGC | CAG | GAG | CAC | CCC | GAA | GCC | GAC | CCA | 2355 |
| Gly | Lys | Tyr | Cys | Arg | Pro | Glu | Ser | Gln | Glu | His | Pro | Glu | Ala | Asp | Pro |      |
|     | 685 |     |     |     |     | 690 |     |     |     |     | 695 |     |     |     |     |      |
| GGT | AGT | GCT | GCC | CCG | TAC | CTG | AAG | ACC | AAG | TTC | ATC | TGT | GTG | ACA | CCA | 2403 |
| Gly | Ser | Ala | Ala | Pro | Tyr | Leu | Lys | Thr | Lys | Phe | Ile | Cys | Val | Thr | Pro |      |
| 700 |     |     |     |     | 705 |     |     |     | 710 |     |     |     |     |     | 715 |      |
| ACG | ACC | TGC | AGC | AAT | ACC | ATT | GAC | CTG | CCG | ATG | TCC | CCC | CGC | ACT | TTA | 2451 |
| Thr | Thr | Cys | Ser | Asn | Thr | Ile | Asp | Leu | Pro | Met | Ser | Pro | Arg | Thr | Leu |      |
|     |     |     |     | 720 |     |     |     |     | 725 |     |     |     | 730 |     |     |      |
| GAT | TCA | TTG | ATG | CAG | TTT | GGA | AAT | AAC | GGT | GAA | GGT | GCT | GAG | CCC | TCA | 2499 |
| Asp | Ser | Leu | Met | Gln | Phe | Gly | Asn | Asn | Gly | Glu | Gly | Ala | Glu | Pro | Ser |      |
|     |     |     | 735 |     |     |     |     | 740 |     |     |     | 745 |     |     |     |      |
| GCA | GGA | GGG | CAG | TTT | GAG | TCG | CTC | ACG | TTT | GAC | ATG | GAT | CTG | ACC | TCG | 2547 |
| Ala | Gly | Gly | Gln | Phe | Glu | Ser | Leu | Thr | Phe | Asp | Met | Asp | Leu | Thr | Ser |      |
|     |     | 750 |     |     |     |     | 755 |     |     |     |     | 760 |     |     |     |      |
| GAG | TGT | GCT | ACC | TCC | CCC | ATG | TGAGGAGCTG | AAACCAGAAG | CTGCAGAGAC |     |     |     |     |     |     | 2598 |
| Glu | Cys | Ala | Thr | Ser | Pro | Met |     |     |     |     |     |     |     |     |     |      |
| 765 |     |     |     |     |     | 770 |     |     |     |     |     |     |     |     |     |      |

GTGACTTGAG ACACCTGCCC CGTGCTCCAC CCCTAAGCAG CCGAACCCCA TATC 2652

( 2 ) INFORMATION FOR SEQ ID NO:9:

( i ) SEQUENCE CHARACTERISTICS:
        ( A ) LENGTH: 770 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Ala | Gln | Trp | Asn | Gln | Leu | Gln | Gln | Leu | Asp | Thr | Arg | Tyr | Leu | Glu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Leu | His | Gln | Leu | Tyr | Ser | Asp | Ser | Phe | Pro | Met | Glu | Leu | Arg | Gln |
|     |     |     | 20  |     |     |     |     | 25  |     |     |     |     | 30  |     |     |
| Phe | Leu | Ala | Pro | Trp | Ile | Glu | Ser | Gln | Asp | Trp | Ala | Tyr | Ala | Ala | Ser |
|     |     |     | 35  |     |     |     |     | 40  |     |     |     |     | 45  |     |     |
| Lys | Glu | Ser | His | Ala | Thr | Leu | Val | Phe | His | Asn | Leu | Leu | Gly | Glu | Ile |
|     | 50  |     |     |     |     | 55  |     |     |     |     | 60  |     |     |     |     |
| Asp | Gln | Gln | Tyr | Ser | Arg | Phe | Leu | Gln | Glu | Ser | Asn | Val | Leu | Tyr | Gln |
| 65  |     |     |     |     | 70  |     |     |     |     | 75  |     |     |     |     | 80  |
| His | Asn | Leu | Arg | Arg | Ile | Lys | Gln | Phe | Leu | Gln | Ser | Arg | Tyr | Leu | Glu |
|     |     |     |     | 85  |     |     |     |     | 90  |     |     |     |     | 95  |     |
| Lys | Pro | Met | Glu | Ile | Ala | Arg | Ile | Val | Ala | Arg | Cys | Leu | Trp | Glu | Glu |
|     |     |     | 100 |     |     |     |     | 105 |     |     |     |     | 110 |     |     |
| Ser | Arg | Leu | Leu | Gln | Thr | Ala | Ala | Thr | Ala | Ala | Gln | Gln | Gly | Gly | Gln |
|     |     |     | 115 |     |     |     |     | 120 |     |     |     |     | 125 |     |     |
| Ala | Asn | His | Pro | Thr | Ala | Ala | Val | Val | Thr | Glu | Lys | Gln | Gln | Met | Leu |
|     |     | 130 |     |     |     |     | 135 |     |     |     |     | 140 |     |     |     |
| Glu | Gln | His | Leu | Gln | Asp | Val | Arg | Lys | Arg | Val | Gln | Asp | Leu | Glu | Gln |
| 145 |     |     |     |     | 150 |     |     |     |     | 155 |     |     |     |     | 160 |
| Lys | Met | Lys | Val | Val | Glu | Asn | Leu | Gln | Asp | Asp | Phe | Asp | Phe | Asn | Tyr |
|     |     |     |     | 165 |     |     |     |     | 170 |     |     |     |     | 175 |     |

```
Lys  Thr  Leu  Lys  Ser  Gln  Gly  Asp  Met  Gln  Asp  Leu  Asn  Gly  Asn  Asn
               180                      185                      190

Gln  Ser  Val  Thr  Arg  Gln  Lys  Met  Gln  Gln  Leu  Glu  Gln  Met  Leu  Thr
          195                      200                      205

Ala  Leu  Asp  Gln  Met  Arg  Arg  Ser  Ile  Val  Ser  Glu  Leu  Ala  Gly  Leu
     210                      215                      220

Leu  Ser  Ala  Met  Glu  Tyr  Val  Gln  Lys  Thr  Leu  Thr  Asp  Glu  Glu  Leu
225                      230                      235                      240

Ala  Asp  Trp  Lys  Arg  Arg  Gln  Gln  Ile  Ala  Cys  Ile  Gly  Gly  Pro  Pro
                    245                      250                      255

Asn  Ile  Cys  Leu  Asp  Arg  Leu  Glu  Asn  Trp  Ile  Thr  Ser  Leu  Ala  Glu
               260                      265                      270

Ser  Gln  Leu  Gln  Thr  Arg  Gln  Gln  Ile  Lys  Lys  Leu  Glu  Glu  Leu  Gln
          275                      280                      285

Gln  Lys  Val  Ser  Tyr  Lys  Gly  Asp  Pro  Ile  Val  Gln  His  Arg  Pro  Met
     290                      295                      300

Leu  Glu  Glu  Arg  Ile  Val  Glu  Leu  Phe  Arg  Asn  Leu  Met  Lys  Ser  Ala
305                      310                      315                      320

Phe  Val  Val  Glu  Arg  Gln  Pro  Cys  Met  Pro  Met  His  Pro  Asp  Arg  Pro
               325                      330                      335

Leu  Val  Ile  Lys  Thr  Gly  Val  Gln  Phe  Thr  Thr  Lys  Val  Arg  Leu  Leu
               340                      345                      350

Val  Lys  Phe  Pro  Glu  Leu  Asn  Tyr  Gln  Leu  Lys  Ile  Lys  Val  Cys  Ile
          355                      360                      365

Asp  Lys  Asp  Ser  Gly  Asp  Val  Ala  Ala  Leu  Arg  Gly  Ser  Arg  Lys  Phe
     370                      375                      380

Asn  Ile  Leu  Gly  Thr  Asn  Thr  Lys  Val  Ile  Asn  Met  Glu  Glu  Ser  Asn
385                      390                      395                      400

Asn  Gly  Ser  Leu  Ser  Ala  Glu  Phe  Lys  His  Leu  Thr  Leu  Arg  Glu  Gln
               405                      410                      415

Arg  Cys  Gly  Asn  Gly  Gly  Arg  Ala  Asn  Cys  Asp  Ala  Ser  Leu  Ile  Val
               420                      425                      430

Thr  Glu  Glu  Leu  His  Leu  Ile  Thr  Phe  Glu  Thr  Glu  Val  Tyr  His  Gln
               435                      440                      445

Gly  Leu  Lys  Ile  Asp  Leu  Glu  Thr  His  Ser  Leu  Pro  Val  Val  Val  Ile
     450                      455                      460

Ser  Asn  Ile  Cys  Gln  Met  Pro  Asn  Ala  Trp  Ala  Ser  Ile  Leu  Trp  Tyr
465                      470                      475                      480

Asn  Met  Leu  Thr  Asn  Asn  Pro  Lys  Asn  Val  Asn  Phe  Phe  Thr  Lys  Pro
               485                      490                      495

Pro  Ile  Gly  Thr  Trp  Asp  Gln  Val  Ala  Glu  Val  Leu  Ser  Trp  Gln  Phe
               500                      505                      510

Ser  Ser  Thr  Thr  Lys  Arg  Gly  Leu  Ser  Ile  Glu  Gln  Leu  Thr  Thr  Leu
          515                      520                      525

Ala  Glu  Lys  Leu  Leu  Gly  Pro  Gly  Val  Asn  Tyr  Ser  Gly  Cys  Gln  Ile
     530                      535                      540

Thr  Trp  Ala  Lys  Phe  Cys  Lys  Glu  Asn  Met  Ala  Gly  Lys  Gly  Phe  Ser
545                      550                      555                      560

Phe  Trp  Val  Trp  Leu  Asp  Asn  Ile  Ile  Asp  Leu  Val  Lys  Lys  Tyr  Ile
               565                      570                      575

Leu  Ala  Leu  Trp  Asn  Glu  Gly  Tyr  Ile  Met  Gly  Phe  Ile  Ser  Lys  Glu
               580                      585                      590

Arg  Glu  Arg  Ala  Ile  Leu  Ser  Thr  Lys  Pro  Pro  Gly  Thr  Phe  Leu  Leu
```

-continued

|  |  |  | 595 |  |  |  |  | 600 |  |  |  |  | 605 |  |
|---|---|---|---|---|---|---|---|---|---|---|---|---|---|---|
| Arg | Phe 610 | Ser | Glu | Ser | Ser | Lys 615 | Glu | Gly | Gly | Val | Thr 620 | Phe | Thr | Trp | Val |
| Glu 625 | Lys | Asp | Ile | Ser | Gly 630 | Lys | Thr | Gln | Ile | Gln 635 | Ser | Val | Glu | Pro | Tyr 640 |
| Thr | Lys | Gln | Gln | Leu 645 | Asn | Asn | Met | Ser | Phe 650 | Ala | Glu | Ile | Ile | Met 655 | Gly |
| Tyr | Lys | Ile | Met 660 | Asp | Ala | Thr | Asn | Ile 665 | Leu | Val | Ser | Pro | Leu 670 | Val | Tyr |
| Leu | Tyr | Pro 675 | Asp | Ile | Pro | Lys | Glu 680 | Glu | Ala | Phe | Gly | Lys 685 | Tyr | Cys | Arg |
| Pro | Glu 690 | Ser | Gln | Glu | His | Pro 695 | Glu | Ala | Asp | Pro | Gly 700 | Ser | Ala | Ala | Pro |
| Tyr 705 | Leu | Lys | Thr | Lys | Phe 710 | Ile | Cys | Val | Thr | Pro 715 | Thr | Thr | Cys | Ser | Asn 720 |
| Thr | Ile | Asp | Leu | Pro 725 | Met | Ser | Pro | Arg | Thr 730 | Leu | Asp | Ser | Leu | Met 735 | Gln |
| Phe | Gly | Asn | Asn 740 | Gly | Glu | Gly | Ala | Glu 745 | Pro | Ser | Ala | Gly | Gly 750 | Gln | Phe |
| Glu | Ser | Leu 755 | Thr | Phe | Asp | Met | Asp 760 | Leu | Thr | Ser | Glu | Cys 765 | Ala | Thr | Ser |
| Pro | Met 770 | | | | | | | | | | | | | | |

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:10:

CCTTCCGGGA ATTC        14

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "degenerate oligonucleotide"

( x i ) SEQUENCE DESCRIPTION: SEQ ID NO:11:

ACNCARATHC ARTCNGT        17

HUMAN ACUTE PHASE RESPONSE FACTOR

This is a division of application No. 08/416,581 filed 4 Apr. 1995 now U.S. Pat. No. 5,719,042.

FIELD OF THE INVENTION

The present invention is related to a novel transcription factor, acute phase response factor (abbreviated APRF hereafter), DNA's encoding it, evaluating and screening methods for searching an inhibitory agent against the function of APRF and an inhibitory agent against the function of the APRF.

More particularly, the present invention is related to APRF which is the transcription factor related to signal transmission of interleukin 6 (abbreviated as IL-6 hereafter) in cells, process for the preparation, DNA's encoding it, replication and expression vector comprising the DNA, host cells transformed or transfected with the replication and expression vector, evaluating and screening method for searching an inhibitory agent against the function of APRF and an inhibitory agent against the function of the APRF.

RELATED ARTS AND PROBLEMS

Bio-signal transmitter mediates the response of cells by transmitting signals stimulated by bioactive substance into cells. In a narrow sense, bio-signal transmitter means a substance which receives a signal from the receptor of a bioactive substance and regulates the expression of the gene in the nucleus. In the bio-signal transmitting substance, a protein which binds nucleus DNA and regulates the expression of the gene was called transcription factor or transcription factor. In this invention, these factors are called transcription factors.

Generally, transcription factors per se are proteins. The transcription factor has a function of transmission of information (signal) to DNA in the nucleus from a primary bioactive mediator to cells, and has a function of regulating the expression of the second protein at the transcription stage. That is, transcription factor mediates in cells when the first bioactive substance acts to cells and the second protein will be expressed. Transcription by the said transcription factor includes to increase (accelerate) the expression and to decrease (restrain) the expression. The second protein regulated its expression by the act of the first protein will be called inducible protein and the gene corresponded to this protein will be called inducible gene in the present invention. For example, the protein induced by IL-6 such as haptoglobin, will be called IL-6 inducing protein and the gene of the said protein such as haptoglobin gene, will be called IL-6 inducible gene.

Example of the proteins promoted their expression by IL-6 are haptoglobin described above, hemopequisin, C-reactive protein, alpha2-macroglobulin, alpha1-acidic glycoprotein, and it is known that these proteins reveal remarkably in acute phase of inflammation. On the contrary, serum albumin is an example of protein suppressed their expression by IL-6.

Transcription substance binds a specific sequence of DNA of inducible gene and regulate the expression of the said inducible gene. Generally, DNA sequence which is bound by transcription factor exists near the promoter region, upstream of the inducible gene. DNA sequence which was bound by the transcription factor is inherent accordance with kinds of the transcription factor. The recent study of the transcription factor is described in Literature 1: Montminy, M., Science, 261, 1694(1993).

Hitherto, NF-IL6 is known as transcription factor related to intracellular signal transmission of IL-6 (See Literature 2: Akira, S et al., EMBO. J. 9, 1897 (1990), Literature 3: Poli, V. et al.;Cell, 63, 643 (1990), Literature 4: Kinoshita, S. et al., Proc. Natl. Acad. Sci. USA, 89, 1473 (1992) etc.).

However, there is no description about the transcription substance which transmits transcription signal to IL-6 inducible gene in nucleus directly from IL-6 receptor in the above literatures. On the other hand, it was known that the sequence: CTGGGA exists upstream of some IL-6 inducible gene. So, some substance which will be activated by IL-6 and bound the said sequence would be suggested in the literature 5: Wegenka, U. M. et al., Mol. Cell. Biol., 13, 276, 1993. But in the literature, existence of the said protein factor was suggested, but the sequence, structure, physical or chemical properties such as molecular weight of the said factor is not clarified. The substance transcription factor APRF per se is not disclosed in the literature.

Transcription substance exists in cells and ordinarily it regulates the transcription of inducible gene by being phosphorylated, moving into nucleus and binding to a proper DNA sequence, when bioactive substance (1st protein) binds to receptor of cells as described hereinbefore. So, substances which can affect the action of the said transcription substance e.g. inhibition, may be used a treating agent for diseases related to the bioactive substance said above.

From above viewpoint, the present inventors aimed IL-6 which is related to inflammatory diseases etc. The present inventors isolated and purified APRF and decided the partial amino acid sequence, cloned the said gene, decided total nucleotide sequence and deduced total amino acid sequence of APRF as transcription factor and obtained APRF per se for the first time as substance.

The present inventors continued the study and established the evaluating and searching method with using APRF for substance which is useful for the treatment of diseases induced by IL-6 such as inflammatory diseases, leukemia, cancer, osteoclasia induced by activated osteoclast, pulmonary hypertension etc. And the present inventors also have been accomplished to obtain the said inhibitor. The present invention is accomplished based on this knowledge.

Techniques for Solving the Problem

The present invention provides substantially purified mammalian transcription factor APRF.

Substantially purified form means, for example, in the case of the polypeptide shown in SEQ ID NO:1 or 5, the polypeptide in a preparation in which more than 90%, e.g. 95%, 98% or 99% of the polypeptide in the preparation is that of the SEQ ID NO:1 or 5.

APRF of the present invention described above have novel primary amino acid sequence. There was no polypeptide having amino acid sequence which is identical to that of the polypeptide of the present invention, when amino acid sequences of the polypeptide was compared by a computer to all known sequences in data base of Swiss Prot (Swiss Prot Release 2.0). Furthermore, there was no nucleotide sequence which is identical to that encoding the polypeptide of the present invention, when the DNA sequence was compared by a computer to all known sequences in data base of GenBank (GenBank Release 70.0).

The detailed description of APRF of the present invention are as follows: About APRF, isolation, purification, decision of the partial amino acid sequence, cloning of cDNA, decision of the sequence of the total amino acid etc. may be carried out by the embodiment method described hereafter. Summary of the method is as follows.

That is, mouse is administered IL-6 and killed 15 min. after administration. Nucleoprotein fraction is extracted from liver. The extract is purified with the column which was fixed DNA oligomer having the following sequence:

CCTTCCGGGAATTC (SEQ ID NO:10)

and purified with electrophoresis on polyacrylamide gel.

The purified product is hydrolyzed with lysyl endopeptidase. Digested products thus obtained are separated with high performance liquid chromatography and each peak is isolated. Amino acid sequence of peptide fragments obtained above are decided from N-terminal by automatic amino acid sequence analyzer.

Corresponding DNA oligomer is synthesized in accordance with the partial amino acid sequence decided above. cDNA of APRF is isolated from mammal cDNA library of liver or placenta with using the DNA oligomer. Amino acid sequence of APRF protein decided from the cDNA sequence of APRF.

In the present invention, examples of mammals are human, mouse, rat etc. APRF in which some amino acid sequence is replaced lacked or inserted may be produced according to the producing tissue or cells although in the same species. The present invention also includes such subtype APRF.

The present invention includes human APRF as an embodiment. Polypeptide having amino acid sequence shown in SEQ ID NO:1, homologue thereof, fragment thereof are included in the present invention concretely.

The present invention provides DNA encoding the above human APRF. The present invention also supplies DNAs having nucleotide sequence shown in SEQ ID NO:2 and 3, DNA's which can be hybridizing to the said DNA's and fragments thereof.

Especially, according to the present invention, (1) a polypeptide having an amino acid sequence shown in SEQ ID NO:1, (2) a DNA encoding the polypeptide described above (1), (3) a DNA having a nucleotide sequence shown in SEQ ID NO:2, and (4) a DNA having a nucleotide sequence shown in SEQ ID NO:3. provide as embodiments.

The present invention includes mouse APRF as an embodiment. Concretely, the present invention includes polypeptide having amino acid sequence shown in SEQ ID NO:5, homologues thereof and fragments thereof.

Further, DNA encoding the said mouse APRF polypeptide is also provided according to the present invention. Concretely, DNAs having each nucleotide sequence shown in SEQ ID NO:6 or 7, DNAs which can be hybridizing to the said nucleotide and fragment thereof will be provided.

Especially, according to the present invention, (5) peptide including amino acid sequence shown in SEQ ID NO:5

(6) a DNA encoding the polypeptide described above (5)

(7) a DNA having a nucleotide sequence shown in SEQ ID NO:6, and (8) a DNA having a nucleotide sequence shown in SEQ ID NO:7 provide as embodiments.

In the present specification, polypeptides described in (1) and (5) having amino acid sequence shown in SEQ ID NO:1 or 5 include not only polypeptides (natural mature protein) having amino acid sequence shown in SEQ ID NO:1 or 5, but also for example, polypeptides which are added proper distinct amino, acids or amino acid sequence less than 20% number of total amino acid shown in SEQ ID NO:1 or 5, preferably less than 5% to N- or C-terminal, derivatives wherein amino acid(s) or amino acid sequence which is not related functionally are changed (deletion, replacement to other amino acid sequence, addition of other amino acid sequence, insertion etc.) including homologues and fragments thereof described hereafter, on the assumption that they possess equivalent biological and pharmacological properties.

A polypeptide homologue of the SEQ ID NO:1 or 5 will be generally over a region of at least 100, preferably at least 150, for example 200, 250 or 300 continuous amino acids, at least 70%, preferably at least 80 or 90% and more preferably at least 95% homologous to the polypeptide shown in SEQ ID NO:1 or 5. Such polypeptide homologues will be referred to below as a polypeptide according to the invention.

Further, fragments of the polypeptide of the present invention will be at least 10, preferably at least 15, for example 20, 25, 30, 40, 50 or 60 amino acids in length, and are also encompassed by the term "a polypeptide according to the invention" as used herein.

Polypeptides except for the polypeptide having amino acid sequences shown in SEQ ID NO:1 or 5 and fragments thereof of the present invention have equivalent properties to the polypeptides having amino acid sequences shown in SEQ ID NO:1 or 5, physiologically or pharmacologically. So, the present invention will provide not only the polypeptide having amino acid sequence shown in SEQ ID NO:1 or 5, but also homologous polypeptides having equivalent properties physiologically or pharmacologically.

A DNA can be hybridized to the DNAs shown in the SEQ ID NO:2, 3, 6 or 7 will be generally over a region of at least 100, preferably at least 150, for example 200, 250 or 300 continuous nucleotide sequence region, at least 70%, preferably at least 80 or 90% and more preferably at least 95% complementary to the DNA shown in SEQ ID NO:2, 3, 6 or 7. Such DNA complements will be referred to below as a DNA according to the invention.

DNA fragments of the present invention means nucleotide part containing at least 10, preferably 15, for example 20, 25, 30 or 40 nucleotide of the DNA of the present invention, and such fragments are equivalent to the DNA of the present invention.

The DNA of the present invention, specified in (2) or (6) includes a group of every nucleotide sequences encoding polypeptides shown in SEQ ID NO:1 or 5.

As known well, there are one to six kinds of codon as that encoding one amino acid (for example, one kind of codon for Methioine (Met), and six kinds of codon for leucine (Leu) are known).

As representative nucleotide sequence encoding amino acid sequence shown in SEQ ID NO:1 or 5, nucleotide sequence shown in SEQ ID NO:2, 3, 6 or 7 may be illustrated. DNAs of the present invention includes DNAs selected voluntary codon without changing amino acid sequence encoding. There is a probability of improving a yield of production of a polypeptide by changing a nucleotide sequence.

The DNA specified in (3) or (7) is the embodiment of DNA shown in (2) or (6), respectively and is sequence in the natural form.

The DNA shown in (4) and (8) indicates the sequence of the DNA specified in (3) or (7) with a non-translational region.

The DNA of the present invention (including fragments thereof, identical hereafter) may be prepared by known methods, for example, gene recombination, chemical synthesis etc. Details of the preparation are illustrated in the following examples. For example, DNAs having nucleotide sequences shown in SEQ ID NOS:3 and 7 may be prepared according to the following methods, that is:

(i) by isolating mRNA from cells which produce the polypeptide of the present invention, (ii) by preparing first strand (single stranded DNA) from mRNA thus obtained, followed by preparing second strand (double stranded DNA) (synthesis of cDNA), (iii) by inserting cDNA thus obtained into a proper plasmid vector, (iv) by transforming host cells with the recombinant DNA thus obtained (preparation of cDNA library), (v) by isolating plasmid containing desired DNA from cDNA library by hybridization method and (vi) by deciding desired nucleotide sequence.

Explained in detail, step (i) can be carried out in accordance with the method of Okayama, H. et al. (described in Methods in Enzymology, vol. 154, p 3, (1987)), or with the method of Chirgwin, J. M. et al. (described in Biochem., 18, 5294 (1979)) using mammalian, for example human or rat, tissue which is thought that APRF is expressed: Preferably, liver, macrophage, placenta tissue cells or cell line can be used.

Steps (ii), (iii) and (iv) are a series of steps for preparing cDNA library, and can be carried out in accordance with the method of Gubler & Hoffman (Gene, vol. 25, pp. 263, 1983) with a slight modification. As examples of the plasmid vector used in the step (iii), many vectors functioning in an E. coli strain (e.g., pBR 322) and in a Bacillus subtilis (e.g., pUB 110) are known, and λ-ZAPII etc. which functions in an E. coli, can be preferably used. In step (iv), any host cells can be used, and DH5 competent cell which has been prepared in accordance with the method described in Gene, 96, 23 (1990), can be preferable used. Recently, cDNA libraries of kinds tissues of animals can be available on the market. For example, cDNA library of mouse liver λ gt 11 and cDNA library of human placenta are on sale from Clontech. The said cDNA libraries on the market can be preferably used.

Step (v) can be carried out by known method per se, for example by plaque hybridization method, colony hybridization method (Gene, 10, 63 (1980)). DNA of APRF of other animals, homologues thereof, fragments thereof are illustrated as suitable probes.

Step (vi) is known per se, it can be carried out according to dideoxy terminator method or Maxam-Gilbert method.

Once the nucleotide sequences shown in SEQ ID NOS:2, 3, 6 and 7 are determined, DNA of the present invention can be obtained by chemical synthesis, by PCR method or by hybridization making use of a fragment of DNA of the present invention, as a probe. Furthermore, DNA of the present invention can be obtained in a desired amount by transforming with a vector DNA inserted a DNA of the present invention into a proper host, followed by culturing the transformant.

A further embodiment of the invention provides replication and expression vectors comprising DNA according to the invention. The vectors can be, for example, plasmid, virus or phage vectors provided with an origin of replication, optionally a promoter for the expression of the said DNA and optionally a regulator of the promoter. The vector may contain one or more selectable marker genes, for example a ampicillin resistance gene.

The present invention also provides host cells transformed or transfected with the vectors for the replication and expression of DNA according to the invention, including the DNA SEQ ID NOS:2, 3, 6 or 7 including the open reading frame thereof. Host cells using in the transformation can be cells of bacteria, yeast, insect or mammals. Transformation can be carried out by each method commonly used.

The polypeptide of the present invention (including fragments thereof, identical hereafter) can be expressed (produced) and accumulated using the said transformant cells which comprises culturing under conditions effective to express. Culturing conditions are well known in accordance with host cells used. Desired polypeptide produced and accumulated intracellular or extracellular of the said transformant cells can be isolated and purified by the common isolation method utilizing the physical, chemical and biological properties of the said polypeptide. Thus, the polypeptide of the present invention i.e. APRF can be prepared with industrial scale. So, the present invention also provides the preparation method of the polypeptide APRF by gene recombination.

The polypeptides of the present invention (e.g. shown in SEQ ID NO:1 or 5) can be prepared by:

(1) isolating and purifying from cultured cells, (2) chemically synthesizing, or (3) gene recombination, preferably, by the method described in (3) for industry.

The preparation of the polypeptide of the present invention by gene recombination can be carried out more preferably, using the expression system (host-vector system) as follows.

For example, the expression in E. coli can be carried out by connecting the DNA encoding the protein (e.g. DNA having nucleotide sequence shown in SEQ ID NO:2 or 6) to the downstream of a proper promoter (e.g., trp promoter, lac promoter, λ PL promoter, T7 promoter etc.), and then inserting it into a vector (e.g., pBR322, pUC18, pUC19 etc.) which functions in an E. coli strain to prepare an expression vector.

Then, an E. coli strain (e.g., E. coli DH1 strain, E. coli JM109 strain, E. coli HB101 strain, etc.) which is transformed with the expression vector thus obtained can be cultured in a proper medium to obtain the desired polypeptide. When a signal peptide of bacteria (e.g., signal peptide of pel B) is utilized, the desired polypeptide can be also produced in periplasm. Furthermore, a fusion protein with other polypeptide can be also produced easily.

Furthermore, the expression in a mammalian cell can be carried out, for example, by inserting the DNA shown in SEQ ID NO:3 or 7 into the downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.) to obtain an expression vector, and transforming a proper mammalian cell (e.g., monkey COS-7 cell, Chinese hamster CHO cell, mouse L cell etc.) with the expression vector thus obtained, and then culturing the transformant in a proper medium to get a desired polypeptide in the culture medium.

As is said above, the polypeptide of the present invention i.e. transcription factor APRF have a function to regulated the transcription related to the intracellular signal transmission by binding a specific DNA part of IL-6 inducible gene in nucleus. So, APRF is useful, for example, for the clarification the diseases induced by the action of IL-6, for the study or development of the said inhibitor for the treatment of the said diseases.

By using the present invention, it can be carried out to search and evaluate an inhibiting substance on the function of APRF. The present invention also provides the screening method for searching inhibiting substance on the function of APRF.

The function of APRF includes being phosphorylated of itself, transition into nucleus, binding to DNA. The said inhibition means inhibition on at least one of the above function of APRF. The present inventors found out that APRF exists in a certain cells, and be activated by phosphorylation when IL-6 acts to the cells. It was known that transcription factor will transit into nucleus and bind to specific DNA sequence, when the factor is phosphorylated. So, the inhibition can be achieved by inhibition on the stage of phosphorylation, on the transition to nucleus or on the expression stage of APRF itself etc.

Further, the present invention also provides an agent containing an inhibitor of the function of APRF, as active ingredient.

The above active ingredient includes, for example, polypeptide having amino acid sequence containing SEQ ID NO:1 or 5, homologues thereof, fragments thereof, antibody obtained from mammals which was immunized homologue or fragment of the said polypeptide, nucleic acid or derivatives thereof which can bind APRF, antisense nucleic acid of APRF gene, expression vector containing antisense nucleic acid, ribozyme which can decompose mRNA of APRF.

APRF antibody which inhibits the function of APRF can be easily prepared in conventional manner, for example, by synthesizing peptide as a proper immunogen in accordance with the amino acid sequence of APRF or the present invention immunizing an animal by administration the peptide.

The antibody obtained above is useful for an inhibitor of the function of APRF and also is important to know behavior of APRF per se in cells or living body. It can be designed lower molecular APRF inhibitor accordance with the recognition part of the said antibody. The present invention includes the said lower molecular APRF inhibitor.

For suppression of the function of APRF, antisense nucleic acid of APRF gene per se or a proper expression vector transfected with the said antisense nucleic acid would be administered to cells or living body. The said antisense nucleic acid or expression vector containing the said antisense can be used as an active ingredient for the inhibitor of the function of APRF of the present invention.

Further, ribozyme which can decompose the mRNA of APRF of the present invention also inhibits the function of APRF, so the ribozyme also can be used as active ingredient of the inhibitor of the function of APRF.

APRF protein or derivative thereof which is partially-modified by gene recombination can be used for complementation or suppression of the function of APRF in cells or living body. The same purpose can be achieved by administration of APRF gene or derivative gene thereof which was partially-modified by gene recombination into cells or living body.

The present invention also provides inhibiting agent containing the inhibitor on the function of APRF of the present invention. The said inhibiting agent may be administered by a proper formulation (administration form) which can be exerted its action in cells or living body. For example, the agent may be prepared as liposome etc. which is modified proper modification on its surface to design the active ingredient can be taken in nucleus directly and it may be administered from proper route accordance with the formulation.

New treating method for diseases induced by IL-6 will be found by using the inhibitor of the present invention.

APRF is newly isolated and assigned by the present inventors as a protein related to intracellular signal transmission of IL-6. On the other hand, in some case, a certain transcription factor also relates transmission of the signals of other bioactive substance. So, the inhibition of APRF may be useful for not only diseases induced by IL-6, but also for diseases induced by other bioactive substance wherein APRF mediates the signal transmission. The present inventors have been found out independently that phosphorylation of APRF is induced by other cytokines other than IL-6, for example, by oncostatin M, leukemia inhibitory factor, interleukin 11, ciliary neurotrophic factor etc. really. The inhibitory agent on the function of APRF, of the present invention also be useful for treatment of diseases induced by the said cytokines.

EXAMPLES

The following examples are illustrated in detail and concretely, but not limit, the present invention.

Example 1

Isolation of APRF

APRF was isolated from nucleus extract of livers of mice which were administered human IL-6 and killed 15 min. after administration.

(1) Isolation of nuclear extract

Nuclear extract was prepared by the method of Wegenka, U. M. et al (Mol. Cell. Biol.,13,276(1993)) with minor modifications.

Mice were administered intravenously human IL-6 (5 $\mu$g/mouse), and killed 15 min. after administration. Mice livers were immediately immunized into ice-cold HANKS solution containing 1 mM orthovanadate. Then the livers were homogenized in homogenization buffer containing 10 mM HEPES (pH 7.6), 0.5 mM spermidine, 0.15 mM spermine, 25 mM KCl, 1 mM EDTA, 1 mM EGTA, 1 mM dithiothreitol (DTT), 1 mM phenylmethylsulfonyl fluoride (PMSF), 10% glycerol with 0.3M sucrose (3 ml per one liver) by 20 strokes in a motor-driven Teflon-glass homogenizer on ice.

Aprotinin (10 $\mu$g/ml), leupeptin (2 $\mu$g/ml), pepstatin (2 $\mu$g/ml), and 1 mM orthovanadate were added prior to homogenization. Nuclei were isolated by centrifugation laying homogenization buffer containing 2M sucrose under the homogenate at 27,000 rpm in an SW28 rotor (Hitachi) for 30 min. at 4° C.

After the supernatant was removed, the nuclei from 10 livers were resuspended in 1 mM of nuclear extraction buffer (50 mM Tris (pH 7.8), 420 mM KCl, 5 mM MgCl2, 0.1 mM EDTA, 2 mM DTT, 0.5 mM PMSF) with protease inhibitors and phosphatase inhibitors. After gentle agitation for 30 min. at 4° C., the mixture was centrifuged at 27,000 rpm in SW28 rotor for 30 min., then the supernatant was subjected to dialysis against dialysis buffer (20 mM HEPES (pH 7.8), 50 mM KCl, 12.5 mM MgCl2, 1 mM EDTA, 1 mM DTT, 1 mM PMSF, 0.1% Nonidet P-40 (BDH Laboratory), 20% glycerol) with protease inhibitors and phosphatase inhibitors. The extract was centrifuged against to remove insoluble precipitates.

(2) Isolation of APRF

The nuclear extracts (from 3000 livers of mice) prepared in (1) were incubated for 30 min. at 4° C., with streptavidin-conjugated paramagnetic beads (Dynabeads M-280 streptavidin, Dynal) containing high-affinity APRF binding site oligonuleotides (5-biothinylatd tandem palindromic APRF consensus sequence, 2×CCTTCCGGGAATTC, SEQ ID NO:10) in the presence of salmon sperm DNA (200 $\mu$g/ml).

Binding proteins were extensively washed with washing solution (20 mM HEPES (pH 7.9), 1 mM EDTA, 5 mM MgCl2, 0.05% NP-40, 10% glycerol) and eluted with washing solution containing 1M KCl. Elutes were immediately diluted with washing solution and again incubated with the magnetic beads with APRF binding sites.

After three rounds of DNA affinity chromatography the elute was separated by SDS-PAGE. Purified product contains 95 kd polypeptide (main band), 85 kd and 70 kd polypeptide (sub band). All the proteins was phosphorylated at tyrosine residue. The proteins were not detected from the extract of cells which were not treated IL-6.

A 95 kd phosphoprotein band was eluted from the gel, precipitated with 10% (v/v) trichloroacetic acid, washed with acetone, and dissolved in a buffer containing 8M urea and 10 mM Tris, pH 9.0. The protein was digested with lysyl endopeptidase for 6 hr. at 37° C. The resulting peptides were separated by reverse-phase high pressure liquid chromatography using a 0.1% (v/v) trifluoroacetic acid and acetonitrile gradient on a 1 mm×25 cm RP-300 column (Applied Biosystems).

The resolved peptides were collected and sequenced by automated Edman degradation on a Applied Biosystems Model 477A sequencer. Amino acid sequence of the peptide was clarified. The fragment was called peptide 3 hereafter. Thr Gln Ile Gln Ser Val Glu Pro Tyr (amino acids 632–640 of SEQ ID NO:1)

Example 2 cDNA Cloning of APRF

An aliquot of phage template DNA from a mouse liver λ gt 11 CDNA library (CLML 1035b; Clontech) was amplified by PCR with a degenerate oligonucleotide:
5'-AC(AGCT)CA(AG)AT(ACT)CA(AG)TC(AGCT)GT-3' (SEQ ID NO:11) from peptide 3 and a λ gt 11 vector reverse primer, and PCR product with a unique DNA sequence which encoded the extract amino acid sequence of peptide 3 was obtained. PCR was carried out for 30 cycles, for 1 min. at 94° C., for 1 min. at 55° C. and for 2 min. at 72° C. as one cycle.

It was confirmed that PCR product having correct amino acid sequence peptide 3 was obtained from the result of subcloning cDNA amplified above into pT7 Blue T vector (Novagen).

Approximately 1.5×10.6 plaques of mouse liver and macrophage λ gt 11 cDNA libraries (alienated from Dr. Shigekazu Nagata of Osaka Bioscience Laboratory), respectively were screened by plaque hybridization using the PCR product as probe.

Hybridization was carried out in 6×SSC adding 5×Denhardt's solution (0.1% Ficoll, 0.1% polyvinylpyrrolidone and 0.1% bovine serum albumin) and 0.5% SDS (sodium dodecyl sulfate), at 65° C. for 15 hr. The filter was washed twice with 2×SSD containing 1% SDS at 65° C. for 30 min.

Positive clones were isolated and sequencing analyzed. Nucleotide sequence of cDNA was analyzed by a dideoxy chain termination method with double strand.

The said positive clone was analyzed as total length cDNA clone of mouse APRF having open reading frame of 2310 bp (shown in SEQ ID NO:6).

The said total nucleotide sequence is shown in SEQ ID NO:7. Amino acid sequence deduced from open reading frame is shown in SEQ ID NO:5.

cDNA of human APRF was isolated using the same probe and the same conditions, by screening a human placental cDNA library (CLHL 1008b; Clontech).

Total length nucleotide sequence and open reading frame nucleotide sequence are shown in SEQ ID NOS:3 and 2, respectively. Amino acid sequence deduced from open reading frame is shown in SEQ ID NO:1.

Example 3

Northern blotting analyses

Total RNA was prepared from mouse tissues by cesium chloride gradiation method. Poly(A)+RNA was purified with Oligo-dT Latex (Oligotex-dT30, Roche). Three μg of poly(A)+RNA was subjected to agarose gel electrophoresis then the RNA was transferred to a nylon membrane (Hybond Plus; Amersham). For human tissues, an RNA blotted membrane (Human Multiple Tissue Northern Blot) was purchased from Clontech.

The membrane was hybridized with a radio labeled DNA probe containing from nucleotide 806 to 1200 of mouse APRF for mouse sample, and 238–726 of human APRF for human samples. The membrane were washed, then dried and autoradiographed. For internal control, the membranes were rehybridized with the actin probe.

What is claimed:

1. An isolated human APRF polypeptide comprising the amino acid sequence of SEQ ID NO:1.

2. A composition comprising the polypeptide of claim 1 and a carrier.

* * * * *